(12) United States Patent
Zucker et al.

(10) Patent No.: US 7,281,285 B2
(45) Date of Patent: Oct. 16, 2007

(54) PEDIATRIC EMERGENCY TRANSPORT DEVICE

(76) Inventors: Stefanie A. Zucker, 3777 Peachtree Rd., #1114, Atlanta, GA (US) 30391; Charles F. Bergh, 5420 Sylmar Ave., #118, Sherman Oaks, CA (US) 91401

( * ) Notice: Subject to any disclaimer, the term of this patent is extended or adjusted under 35 U.S.C. 154(b) by 22 days.

(21) Appl. No.: 11/117,279

(22) Filed: Apr. 28, 2005

(65) Prior Publication Data

US 2005/0193491 A1 Sep. 8, 2005

Related U.S. Application Data

(63) Continuation-in-part of application No. 10/238,754, filed on Sep. 10, 2002, now Pat. No. 6,898,811.

(60) Provisional application No. 60/566,000, filed on Apr. 28, 2004, provisional application No. 60/662,653, filed on Mar. 17, 2005.

(51) Int. Cl.
*A61G 1/044* (2006.01)
(52) U.S. Cl. ............... 5/626; 5/655; 5/603; 5/487; 297/219.12
(58) Field of Classification Search ............ 5/626, 5/655, 603, 484, 487; 297/219.12
See application file for complete search history.

(56) References Cited

U.S. PATENT DOCUMENTS

| | | | | |
|---|---|---|---|---|
| 2,787,506 A | * | 4/1957 | Travisano | ............... 5/610 |
| 4,627,426 A | * | 12/1986 | Wegener et al. | ............ 604/356 |
| 4,882,213 A | * | 11/1989 | Gaddis et al. | ............. 428/136 |
| 4,883,701 A | * | 11/1989 | Rankin et al. | ............. 428/136 |
| 4,885,200 A | * | 12/1989 | Perdelwitz et al. | ......... 428/136 |
| 4,886,697 A | * | 12/1989 | Perdelwitz et al. | ......... 428/192 |
| 4,891,454 A | * | 1/1990 | Perdelwitz et al. | ......... 428/137 |
| 4,892,769 A | * | 1/1990 | Perdelwitz et al. | ........... 428/68 |
| 6,093,895 A | * | 7/2000 | Niosi | ........................ 177/136 |
| 6,377,177 B1 | * | 4/2002 | Broussard et al. | ....... 340/573.1 |
| 6,493,890 B2 | * | 12/2002 | Smeed | ....................... 5/503.1 |

FOREIGN PATENT DOCUMENTS

| | | | |
|---|---|---|---|
| FR | 2810221 | * | 12/2001 |
| WO | WO9321871 | * | 11/1993 |

* cited by examiner

*Primary Examiner*—Sunil Singh
(74) *Attorney, Agent, or Firm*—Withers & Keys, LLC

(57) ABSTRACT

A device for emergency transport of pediatric patients that safely and efficiently transports a pediatric patient to a medical facility is described. The device enables the transport of pediatric trauma patients on a conventional stretcher while still enabling a backboard to be used therewith to immobilize a critically-injured patient. Additionally, the device provides for more comfortable and sanitary transport of a pediatric patient by adding a disposable padded cushion, which is placed on the device prior to placing the child in the device for emergency transport.

4 Claims, 25 Drawing Sheets

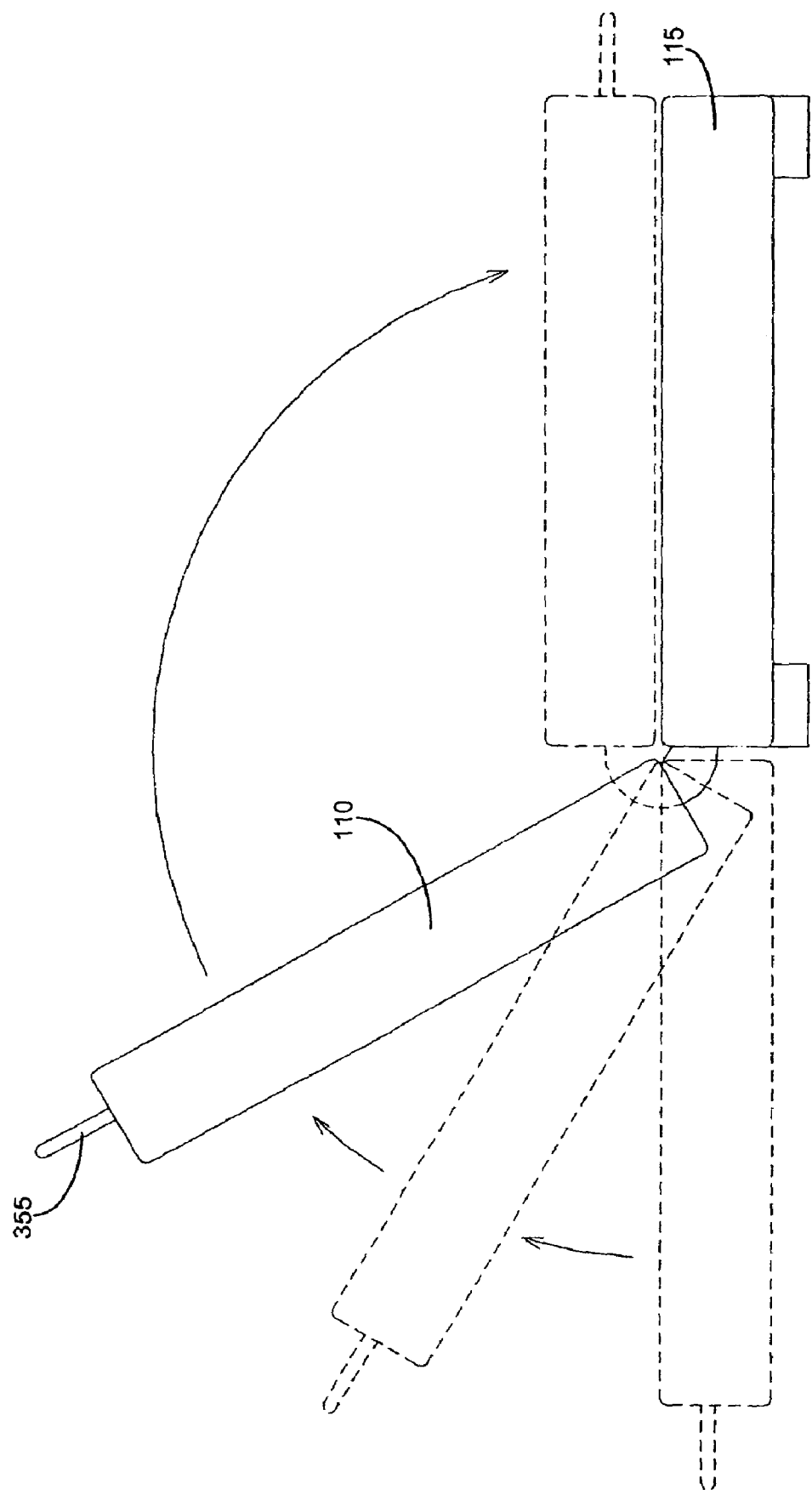

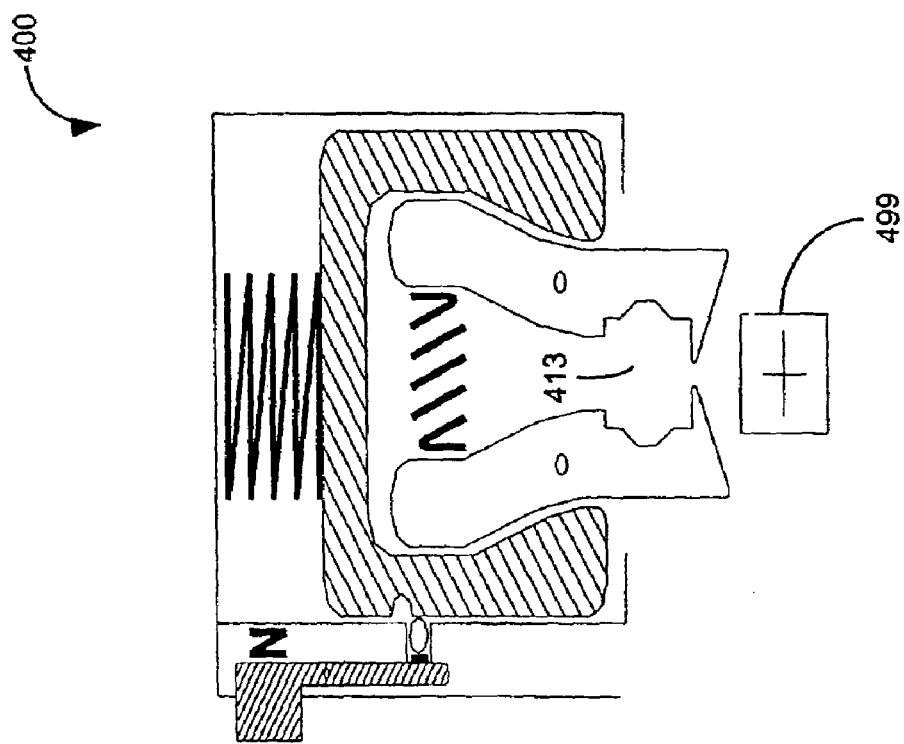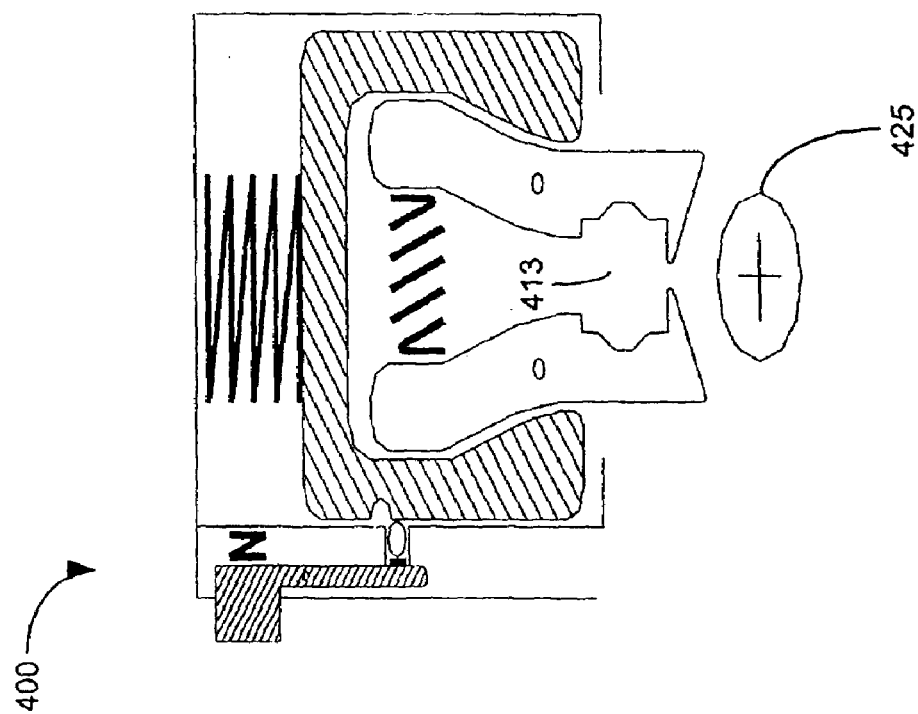
FIG. 4D

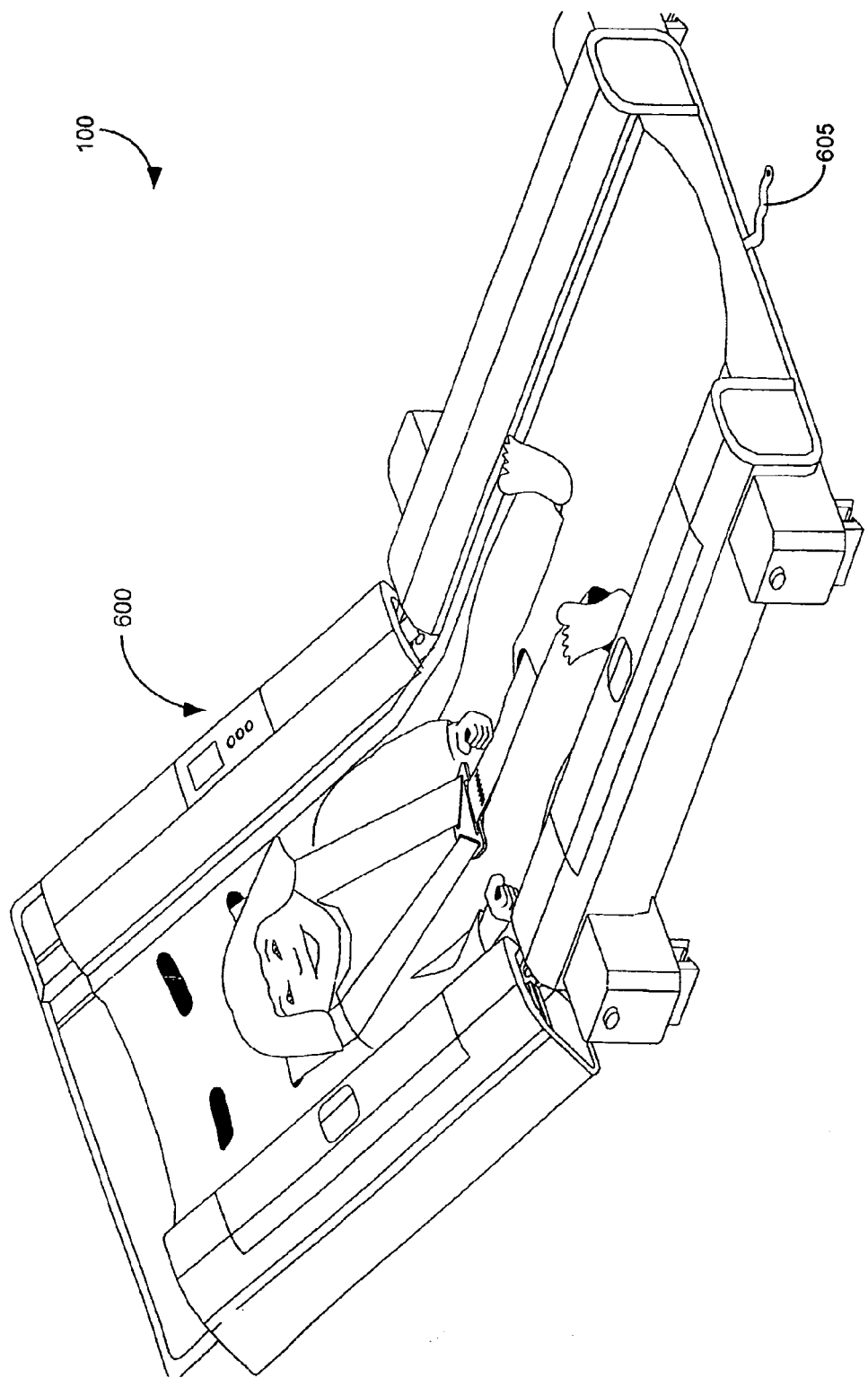

PEDIATRIC EMERGENCY TRANSPORT DEVICE

CROSS REFERENCE TO RELATED CASES

This application is a continuation-in-part of U.S. patent application 10/238,754, filed on Sep. 10, 2002, now U.S. Pat. No. 6,898,811, entitled "Device for Emergency Transport of Pediatric Patients," and claims the benefit of priority to (i) U.S. provisional patent application no. 60/566,000, filed on Apr. 28, 2004 and entitled "Emergency Pediatric Transport with Backboard," and (ii) U.S. provisional patent application no. 60/662,653, filed on Mar. 17, 2005; and entitled "Emergency Pediatric Transport with Liner." Each of the above patents and patent applications is incorporated in its entirety by reference as if set forth in full herein.

BACKGROUND OF THE INVENTION

1. Technical Field

The invention relates in general to the fields of emergency transport devices and, more particularly, to a device for emergency transport of pediatric patients adapted to engage rails of a conventional stretcher, and accessories therefor.

2. Description of the Related Art

Medical personnel, such as emergency medical technicians, often transport injured children to and between medical facilities. During transport, medical personnel may be required to stabilize injured children using either medical equipment such as EKG's or Intravenous Lines or via hands-on procedures such as cardiopulmonary resuscitation. To avoid further injuring these children, medical personnel must transport them using safe equipment. Consequently, medical personnel need both a safe way to transport children and the flexibility of performing a variety of medical procedures, as needed.

In addition to those needs, medical personnel may also transport individuals ranging in age from a newborn baby to an elderly individual. To accommodate such a diverse group, medical personnel require the ability to effectively secure both adults and children during transport. It is, however, the ability to safely and effectively transport small children that causes the greatest challenge to the medical professional. For example, a seven-pound, eighteen-inch newborn baby differs significantly from a thirty-pound, forty-inch child. As a result, the transport equipment must accommodate children of varying size. Because this equipment may be used when the lives of these individuals are failing, it should operate efficiently. In addition, space limitations in an ambulance, for example, demand easy storage for this equipment. Therefore, medical personnel need equipment that adjusts to children of varying size, operates efficiently, and stores easily.

In response to some of the above-listed needs, medical personnel currently transport children by securing them via various means to a stretcher. One method is accomplished by securing the child directly to the stretcher via use of the stretcher's straps (using the same method they would use to secure and adult). This method uses a typical stretcher that operates efficiently and stores easily. Yet, typical or conventional stretchers do not transport children safely. Usually medical personnel cannot apply enough tension to the straps to safely restrain a child. In addition, the location of the straps may impair medical personnel from performing lifesaving procedures. Additionally, since a small child may be still somewhat mobile, they are at risk of incurring additional injuries during the transport. As a consequence, strapping a child directly to a stretcher does not adequately meet the needs of medical personnel.

Similarly, strapping a mother who holds a child to a stretcher does not satisfy the above-mentioned needs. Though this technique uses equipment that operates efficiently and stores easily, it hinders safe transport. If the ambulance stops suddenly and the mother releases the child, the child may "fly forward" in the ambulance causing further injury. If the mother is successful in "holding on" to her child, the child can still be injured, if the mother's weight is thrown forward crushing the child against the seatbelt. In addition, the technique of "holding the child" accommodates children of varying size only to the extent that the mother can hold them. Finally, because the mother's hands cover a portion of the child, she impairs the administration of medical treatment on that area. Thus, strapping a mother with child fails to meet the needs of medical personnel.

Further, strapping a typical car seat that holds a child to a stretcher also fails to meet the needs of medical personnel. Though the car seat can adapt to children of varying size, this method impairs safe transport. Since the seat belts in an automobile differ from the straps on a stretcher, and the shape of a car seat differs from the shape of a stretcher, the car seat does not attach securely to the stretcher. This lack of security threatens safety by creating the potential for the car seat to shift or come loose during transport. In addition, the car seat impairs the administration of medical procedures. For example, a paramedic may need to administer cardiopulmonary resuscitation (CPR). Since a child in the car seat cannot lay flat, the paramedic must remove the child from the car seat and begin compressions with the child in his arms. By removing the child from the seat, medical personnel threaten the safety of the child.

In response to the failures of the above-mentioned techniques for transporting injured children, alternative types of pediatric restraining devices have been developed. For example, one device secures to a stretcher using straps. It includes a bendable support mattress secured in a given angular position by leg supports. Medical personnel secure the injured child to the support mattress after this device is attached to the stretcher. While this device provides some improvement, it impairs administration of CPR. In addition, connecting this device to the stretcher using belts demands that medical personnel spend additional time securing the device.

Another pediatric device provides a hard frame with rotating side panels. It attaches to a stretcher with straps and stores in a collapsed position. Though the collapsibility feature enables easy storage, this pediatric device is difficult to attach to the stretcher. Medical personnel sacrifice time in securing the device to the stretcher. In addition, using straps create the potential that the device may move during transport. This potential movement can hinder performance of lifesaving medical procedures. Although this device includes a restraining feature that confines the child to the device, this feature does not adjust to children of varying size.

In sum, previous pediatric emergency transport devices do not transport safely, enable performance of medical procedures, operate efficiently, adapt to children of varying size, and store easily. Therefore, they do not satisfy all of the needs of medical personnel. When responding to a call, medical personnel should be equipped adequately to provide the medical attention necessary to stabilize and transport any type of patient, including children. They must gather the equipment needed and provide the required medical treatment, including CPR, in a limited amount of time. Thus, there is a need for a device for the emergency transport of pediatric patients that satisfies all of the above-mentioned needs.

Yet further, when a child is critically injured, (i.e. a head or neck injury, or typically any injury where a child has lost consciousness and there is the potential that a spinal injury may have occurred) emergency medical technicians must immobilize the patient, often securing the neck first with a cervical collar, and then the entire body to a rigid surface (typically a backboard) to prevent movement that could cause further injury to the neck or spinal column. Currently, such backboards are then secured onto a stretcher via straps, and the child is transported in an ambulance (or depending on the severity of injury, airlifted via Life-Flight helicopter) to an emergency care facility. Treatment is provided en-route to the facility by the on-board EMT or paramedic. This procedure, while effective, can still be improved upon.

Additionally, to treat a pediatric patient, medical technicians must use pediatric supplies (i.e. Pulse-Ox equipment, IV catheters, intubation tubes, etc.) on a pediatric patient. Unless the vehicle dispatched is from a child-specific emergency facility, these supplies are often mixed in with adult supplies, and precious life-saving seconds can be wasted, trying to locate them during a trauma call. Additionally, medical technicians today must rely on either the parent or doctor to provide accurate weight information prior to the transport, or the use of a Broselow tape if one is available, to estimate the weight of a child in order to administer medications at the proper dosages. Lack of accurate weight information may lead an emergency technician to under or over-medicate the pediatric patient. Therefore, while an emergency technician who secures a pediatric patient to a backboard may now have the ability to secure a pediatric patient safely for transport, such technician does not have an efficient means of accessing pediatric supplies for treatment en-route or obtaining accurate weight information to properly administer medications. The device of the present invention not only allows a medical technician quickly to access all pediatric supplies from a single location and obtain an accurate measurement of a pediatric patient's weight, it also enables immobilization of the pediatric patient on a backboard.

An additional challenge to transporting a pediatric patient is comfort and sanitation. A child being transported in an emergency situation is often frightened and may often have an injury that causes the release of bodily fluids. In some embodiments, the device of the present invention can be designed primarily with safety in mind, rather than comfort. Such an embodiment includes only minimal padding to ensure that life-saving procedures can be provided directly on the device, without removing the pediatric patient from the restraints. Such minimal padding is not designed to be cushioned, nor to resist the transfer of bodily fluids. Therefore there is a need for another embodiment of the present invention in which an additional pad can be placed between the child and the device to provide an extra measure of comfort to a child in an already stressful situation, as well as to resist the transfer of any bodily fluids that may be secreted. Preferably, such additional pad will not interfere with use of the device's existing harness restraint system and may be easily removed by the emergency technician, without removing the restraints from the child, should life saving measures be required en-route.

SUMMARY OF THE INVENTION

The present invention satisfies the above-mentioned needs in a device for the emergency transport of pediatric patients that clamps to the side rails of the various conventional ambulance stretchers. The device effectively aids in the administration of medical procedures on injured children. To accomplish this, it includes a data center that measures individual information about a child (e.g. weight and heart rate). Using the data center medical personnel can prescribe the appropriate medicine dosage and evaluate the child's stability without additional equipment. The rigidity of the frame also reduces equipment needed for the administration of cardiopulmonary resuscitation (CPR). Instead of using a backboard, medical personnel can administer CPR to a child without removing them from the device. Consequently, the invention reduces the additional equipment needed in administering medical procedures.

A further advantage includes increasing the operating efficiency of medical personnel. The subject invention includes multiple single-action components that reduce the time expended in using the device. The use of a snap-on/ quick-release, single-action clamp mechanism, reduces the time needed to secure the device to a stretcher, allowing medical personnel to focus more on the injured child. In addition, the multi-purpose clamp mechanism of the invention enables the device to attach to objects of varying shapes and widths providing increased utility. Therefore, although multiple stretcher devices are currently in use in the marketplace, medical personnel need carry only one pediatric transport device to ensure coverage of all sizes of children. The invention increases efficiency by reducing the equipment needed for transport and the time associated with utilizing that equipment.

This present invention also presents medical personnel with a number of other advantages, including easy storage. The invention collapses enabling it to be stored in an alcove in the ambulance or mounted on the ambulance wall. In addition to easy storage, the invention includes a uniquely designed restraint that reduces the probability of accidental release. The advantages of this restraint lie in its increasing safety by avoiding accidental release even when confining children of various sizes. Many other advantages and useful techniques for the subject invention will become apparent to those skilled in the art.

Generally described, the present invention is a device for the emergency transport of pediatric patients that can be used with a stretcher with a rail to transport a patient. The invention includes a frame adapted to receive a patient and a snap-on/quick release clamp mechanism connected to the frame. The invention's clamp mechanism is adaptable to connect to stretchers of various widths and sizes. The invention may also include a hinge assembly connected to the two frame members. The hinge assembly permits relative rotation of the two frame members. More specifically, the hinge assembly may include an actuation device that selectively adjusts the relative rotation of the frame members.

According to one aspect of the invention, the device includes a restraining belt assembly with a single-action release that connects to both frame members. The restraining belt assembly secures the patient to the stretcher when engaged. More specifically, the restraining belt assembly may include two belts each of which can be released easily and couples to the first frame member at one end and attaches to a common connector at the other end. Each belt may include a length adjustment. The first frame member may also include first and second sets of openings. The belts may be coupled to the first set of openings in response to the patient being placed in the device. The restraining belt assembly, hinge assembly and clamp may also include a release to disengage by a single action.

The clamp mechanism may include a quick-release universal grasping device with a groove that couples to the rail with either a circular or rectangular shape. The clamp mechanism may also include a housing member, a cam, and a locking device. The cam extends close to the grasping device and can connect to the housing member through a spring. When the grasping device contacts the cam, it moves within the housing member. The locking device places the cam in a lock position when engaged. The locking device may include a locking ball detent that can connect to a portion of the cam and a release that can connect to the locking ball detent. When the release is pressed, it disconnects the locking ball detent from the cam, which releases the cam from the lock position. The clamp may adapt to accommodate stretchers of varying width.

The hinge frame may couple to a first part of the first frame member and a first part of the second frame member. The actuation device may include a lever that connects to a second part of the first member and a locking pin that selectively engages the hinge frame in a plurality of positions. A cable connects the locking pin to the lever, such that the locking pin disengages the openings when the lever is actuated.

This present invention may also include a data acquisition device that measures the weight of a person. In addition, the invention may include a handle that connects to a frame member, storage devices that connect to a frame member, and a pad that extends longitudinally over both frame members. The invention may also include second, third and fourth clamps where the second clamp is positioned proximate to the first clamp. The third and fourth clamps diametrically oppose the first and second clamps, respectively. The invention may also include a second hinge assembly that permits relative rotation of a second side of the frame members. The second hinge assembly includes a second hinge frame diametrically opposed from the first hinge frame. A second cable connects the second locking pin to the lever, which enables the second locking pin to engage the second hinge frame in a plurality of positions when the lever is actuated.

The present invention also provides a quick-release universal clamp that couples to objects having either a circular or rectangular shape. The clamp includes a housing member, a grasping device with a groove to receive the object, and a cam surrounding a portion of the grasping device. By contacting the cam when coupled to the object, the grasping device displaces the cam within the housing member. The universal clamp may attach to this present invention.

In a preferred embodiment of the present invention, the transport device is able to accept or receive a commercially available, off-the-shelf pediatric backboard for attachment. Within the scope of the invention, the device may also be configured to accept an adult backboard. The frame of the device is preferably configured to have a ledge within the interior of the device, on which the backboard may rest. In an alternative implementation, such a backboard is placed on a channel or set of brackets within the device, upon which the backboard will sit. Other alternative implementations may apply. Cantilever clamps or any other locking mechanism, such as a locking pin, or slide-in pin, etc. known to those skilled in the art may be used to secure the backboard tightly in place within or on the pediatric transport device.

Preferably, these clamps or other such locking mechanisms, when not in use, are designed to lock into place out of the way of the central padded portion of the transport device.

The present invention also provides for the incorporation of a single-use, disposable cushion of similar dimensions as the interior of the pediatric transport device to be placed between the child and the receiving surface of the device. The cushion provides comfort and acts as a sterile barrier during the transport. Preferably, the cushion includes either a single compressible material or several layers of such material, as will be appreciated by those skilled in the art. In a preferred embodiment the cushion is made of an absorbent material, which absorbs bodily fluids. In an alternative embodiment, the cushion is made of a non-absorbent material, which impedes the transfer of bodily fluids. In both of the above embodiments, the cushion acts as a barrier to resist the transfer of bodily fluids and germs from the patient to the device. Preferably, the cushion includes a number of pre-made cuts and/or slit locations matching the locations required to pass through the shoulder and leg harness restraints of the device. In one embodiment, the cushion is perforated vertically down the center from top to bottom to allow for rapid removal when life-saving procedures are required or upon completion of an emergency transport.

BRIEF DESCRIPTION OF THE DRAWINGS

FIG. 3C is a side view illustrating collapsibility feature of the device of FIG. 1;

FIG. 4D is a planar view illustrating the versatility of the clamp mechanism to accommodate two types of stretcher railings;

FIG. 6 is a perspective view illustrating a data acquisition device and a closure strap;

Figure 1:
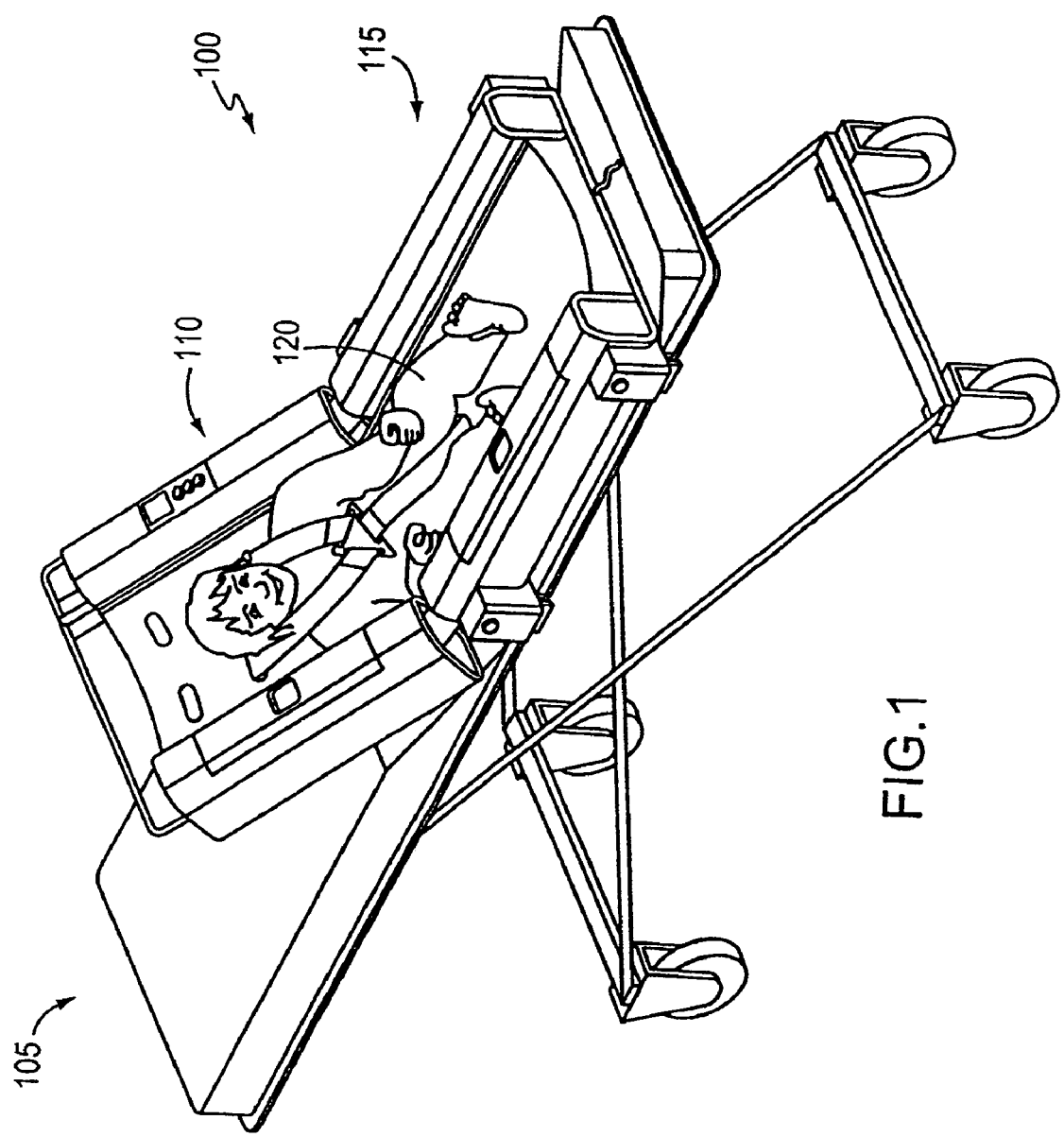
FIG. 1 is a perspective view of a device for emergency transport of pediatric patients according to an exemplary embodiment of the invention, which is shown in greater detail in FIGS. 2A-12.

While the invention is susceptible to various modifications and alternative forms, specific embodiments have been shown by way of example in the drawings and are described in detail. It should be understood, however, that the description herein of specific embodiments is not intended to limit the invention to the particular forms disclosed. On the contrary, the intention is to cover all modifications, equivalents, and alternatives falling within the spirit and scope of the invention as defined by the appended claims.

DETAILED DESCRIPTION OF EMBODIMENTS OF THE INVENTION

Illustrative embodiments of the invention are described below as they might be employed in a device for emergency transport of pediatric patients. In the interest of conciseness, not all features of an actual implementation are described in this specification. It will of course be appreciated that in the development of any actual embodiment, numerous implementation-specific decisions must be made to achieve the developer's specific goals, such as compliance with system-related, business-related, and law-related constraints. Moreover, it will be appreciated that even if such a development effort might be complex and time-consuming, it would nevertheless be a routine undertaking for one of ordinary skill having the benefit of this disclosure.

1. Overview

The present invention describes a device for emergency transport of pediatric patients that safely and efficiently transports a pediatric patient to a medical facility. The device preferably attaches to a conventional transport device, such as a stretcher. The transport device typically is positioned in the center of the stretcher to maximize stretcher stability—although there may be occasions or situations in which it is preferable for the invention to be positioned elsewhere on the stretcher.

This present invention includes a frame that receives the patient. The frame is preferably divided into sections. For example, an upper section of the frame is designed to support the patient from head to waist. Conversely, a lower section is preferably designed to support the patient from waist to feet. These sections preferably are constructed of metal tubing, medical-grade plastic, or some combination of each.

To confine the patient to the transport device, a child restraint in the form of a restraining belt assembly is used. The restraining belt assembly preferably includes two shoulder belts and a leg belt. A waist belt is optionally used to connect into the center of the belt assembly to create a five-point harness in conventional manner. The belts may be formed from nylon, for example. In addition, the two shoulder belts preferably include a horizontal strap that connects them to each other. This strap helps prevent a child from removing an arm from the shoulder belts. Preferably, the shoulder belts connect to the frame using quick-release buckles. The buckles are preferably formed from stainless steel covered with a plastic-like material. In contrast to the shoulder belts, the leg belt preferably attaches directly to the frame. Though the shoulder belts and leg belt connect to the frame, a metal connector joins the other ends of the three belts together. If desired, the metal connector can include a label having a children's cartoon character shown thereupon.

Further, the transport device is designed to accommodate children of various sizes using the restraining belt assembly. The upper section of the frame includes several sets of openings associated with ranges of physical dimensions. After placing a child in the device, medical personnel restrain the child by securing the buckles to the set of openings that best accommodate the child's size. To further accommodate the size of the child, medical personnel may vary the length adjusts included on the shoulder and leg belts from the front of the device, without removing the child from the seat or the seat from the stretcher. The length adjusts themselves may be formed from metal covered in plastic material.

Medical personnel secure a child to the transport device by connecting the buckles to a set of frame openings. Specifically, the buckles are pushed or pressed toward the openings. Each opening contains therein an anchor that is centered within the opening; such anchor is preferably formed from stainless steel. As the buckle approaches the anchor, it contacts a locking plate within the buckle, also preferably formed from stainless steel. The locking plate rotates slightly and then traps the anchor. This action secures the restraining belt assembly to the frame. Hence, it secures the child to the transport device of the present invention. Securing the buckles to the frame above the child's shoulders reduces the chance of accidental release during transport.

Conversely, the single action of pressing a release button and pulling the buckles away releases a child from the transport device. Specifically, pressing the release button rotates the locking plate. As the buckle is pulled away, the anchor clears the locking plate and removes the restraint. Similarly, the single action of attaching the buckle engages the restraining belt assembly. Hence, the restraining belt assembly is considered to be a single action device.

In addition to the restraining belt assembly, the invention includes a hinge assembly. Such hinge assembly controls the rotation of the upper frame section relative to the lower frame section. The hinge assembly includes a hinge frame and an actuation device. The hinge frame connects the hinge assembly to the frame sections and may be formed from stainless steel. The actuation device controls the movement of the upper section relative to the lower section and includes a cable, lever, and locking pin that selectively locks within the hinge frame. The cable and the lever are preferably formed from braided steel and stainless steel, respectively. Alternatively, the actuation device includes a pressure clamp and ball-ratchet instead of the locking pin.

To operate the hinge assembly, medical personnel squeeze the lever. This action unlocks the locking pin from the hinge frame. With the lever still squeezed, the upper section is manually rotated to a desired angular position. Releasing the lever selectively secures the locking pin in the hinge frame and retains the upper section in the desired position. The single action of releasing the lever engages the hinge assembly. In addition, the single action of squeezing the lever disengages the hinge assembly. Hence, the hinge assembly is also considered to be a single action device.

The transport device also includes a clamp mechanism with at least one quick-release clamp that attaches to a rail of an object such as a stretcher. Numerous clamps also may be used. The clamp includes a housing member, grasping device, cam and locking device. The grasping device connects the stretcher by receiving its rail. Alternatively, the grasping device may connect the transport device to a wall of an ambulance or any other object having a rail or post. The locking device secures the rail within the grasping device through interaction with the cam. The locking device includes a locking ball detent, pressure clamp, or similar securing device. The clamp components preferably are constructed of stainless steel.

To operate the clamp, medical personnel push the transport device with the grasping device (e.g., clamp) extended towards the rail or handle of the stretcher. As the grasping device contacts the rail, the grasping device pivots and contacts the cam. In response, the cam moves upward in the housing member and creates a spring force. Once the grasping device surrounds the rail, the spring force moves the cam downward in the housing member. Medical personnel then pull up slightly on the device. As they pull up, the cam floats further downward in the housing member. As the cam approaches the locking device, it engages and secures the cam in a locked position. The securing of the cam results in securing the grasping device in a locked position, which secures the clamp and, hence, the transport device to the stretcher.

To release the clamp, medical personnel press a release included within the locking device. This action disengages the locking device from securing the cam. Then, medical personnel pull the transport device away from the rail of the stretcher. As the rail moves within the grasping device, it contacts the cam. The cam moves upward in the housing member creating a spring force. Once the rail clears the grasping device, the cam moves downward in the housing member as the spring force releases. The cam returns to its original position.

To increase efficiency, the clamp includes a width accommodation feature and universality feature. Medical personnel are able to use the width accommodation feature by displacing the clamp relative to the frame. For example, medical personnel adjust the clamp for narrower stretchers by pushing the clamp further inside the frame. The universality feature enables the clamp to attach to rails of various shapes. Because the grasping device includes a universal groove, medical personnel attach the transport device to stretchers with circular rails in the same manner by which they attach them to stretchers with rectangular rails. Thus no additional equipment or training is needed. Alternatively, the universality feature may include other shapes, such as triangular.

In another embodiment of the present invention, the interior section of the transport device has been adapted to accommodate placement of a commercially available off-the-shelf pediatric backboard within the frame. In an alternative embodiment, the interior section of the transport device has been adapted to accommodate placement of an adult backboard within the frame. Each side of the device frame preferably includes one or more ledges or brackets that extend towards the interior of the transport device just above the level of the pad. The backboard is able to rest on these ledges covering the central padded portion of the transport device. The ledges may be formed of the same material as the frame.

In an alternative embodiment, the transport device includes the two (2) channels defined within either side of the frame, into which the backboard may slide and rest. The transport device preferably includes cantilever clamps, or another such locking mechanism (such as a slide-in pin, locking pin, or the like), to secure the backboard rigidly in place. Preferably, these clamps or other such locking mechanisms, when not in use, are designed to lock into place within the side of the frame when not in use.

In use, medical personnel preferably first secure the patient on a commercially available backboard. Medical personnel are also able to attach the emergency transport device to a stretcher via the single-action clamps described previously. To lock the backboard into the transport device, medical personnel may simply place the backboard within the central portion of the device, either resting on the ledges or within the channels previously described or via a similar implementation. A cantilever clamp or slide in pin or similar locking mechanism is then used to secure the backboard within the frame. One or more clamps may be used to secure the backboard rigidly in place. Usage of cantilever clamps and other such similar locking mechanisms will be familiar to those with ordinary skill in this area and, as such, are not described in detail herein.

A cushion is also provided for one-time use during transport of a pediatric patient to provide a sterile, but comfortable barrier between the patient and the device. In one embodiment, the cushion is made out of two layers of a paper or similar disposable material with a compressible, disposable absorbent material located in-between. Alternatively, the cushion is made out of a single compressible absorbent material. In another alternative embodiment, the cushion is made of a non-absorbent material, which impedes the transfer of bodily fluids. The cushions may either be packaged individually, or may be bound together as a roll, to be torn-apart into separate units as needed.

The cushion is preferably made to conform to the interior dimensions of the pediatric transport device (e.g., the receiving surface of the frame portion of the device) and preferably includes cut-out sections that directly align with the restraining belt anchors on the transport device to accommodate the insertion of the harness restraint buckles above the shoulders of the child as well as a cut-out section that aligns with the fixed restraining belt location between the legs of the child. The cushion preferably also has a perforation running directly down its center from top to bottom to allow it to be quickly and easily "torn-off" should life-saving measures be required. Use of the cushion requires little to no expertise on the part of the medical technician. It is placed on the device after the device is secured to the stretcher. The child is then placed in the device on top of the cushion and the restraining belt assembly is attached directly to the device through the cushion cut-out sections. After use by a single pediatric patient, the cushion is disposed of with all other bio-related material.

2. Description of the Drawings

Referring now to the drawings, in which like numerals indicate like elements throughout several figures, FIG. 1 illustrates a perspective view of a device 100 for emergency transport of pediatric patients according to an embodiment of the invention. The device 100 for emergency transport of pediatric patients provides safe transport of a youth and may attach to a transport device 105, such as a stretcher. The device 100 includes a frame divided into a pair of sections 110, 115. The contours of these frame sections form a receptacle for a child 120. The sections 110, 115 may support the upper and lower portions of the child 120, respectively.

Figure 2A:
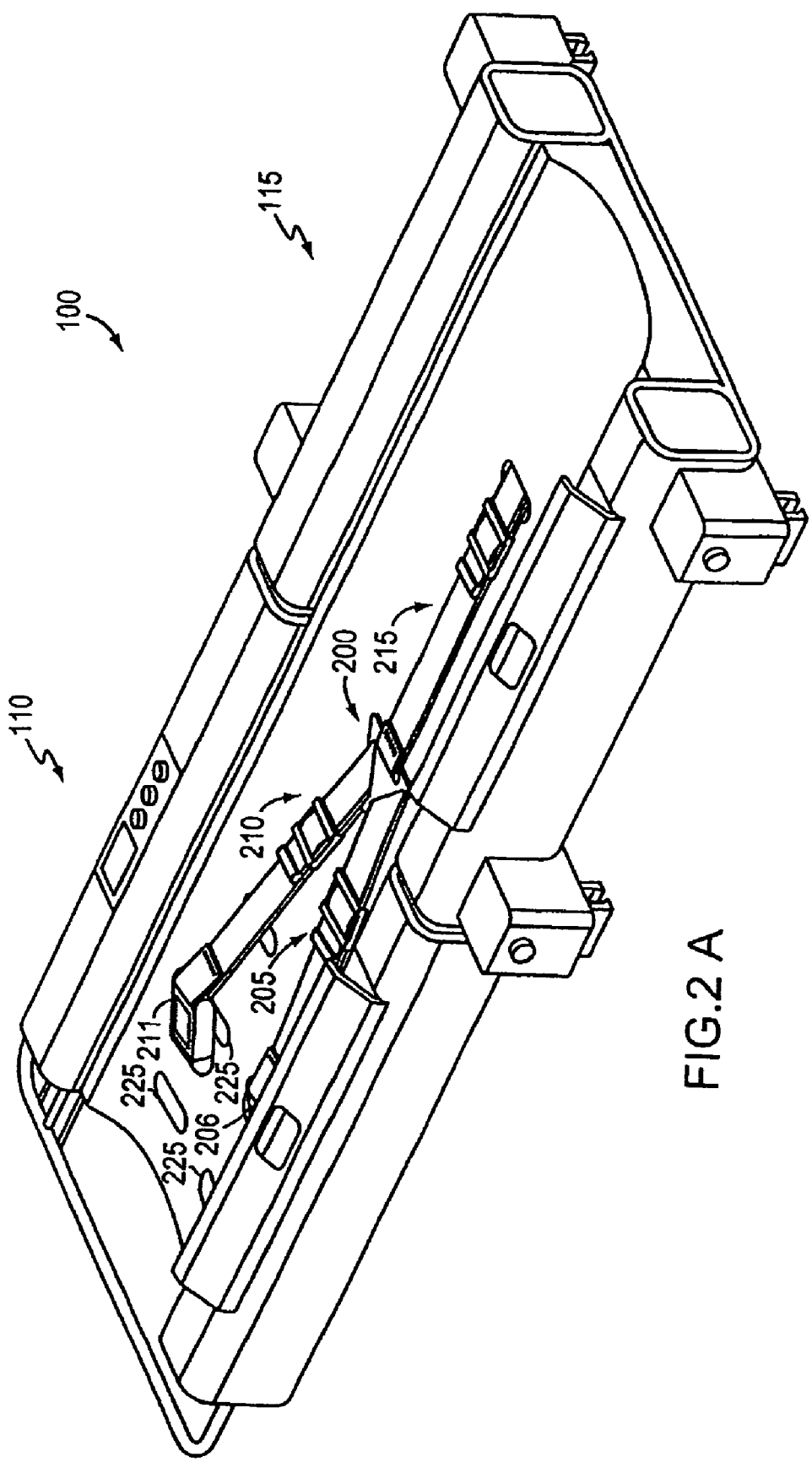
FIG. 2A is a perspective view illustrating the integration of a restraining belt assembly within the pediatric emergency transport system of FIG. 1.

FIG. 2A is a perspective view illustrating the integration of a restraining belt assembly 200 that releasably secures a child to the device 100. The restraining belt assembly 200 includes the belts 205, 210, 215 and the buckles 206, 211. It accommodates children over a wide range of sizes by using a multi-level adjustment feature. The section 110 includes several sets of orifices 225 (of which three have been shown) in which the buckles 206, 211 may be inserted to connect the buckles to the device. Associated with each set of orifices 225 is a range of physical dimensions for a child. For example, medical personnel may use one set of orifices 225 for children ranging from ten to twenty inches tall. By connecting the buckles 206, 211 to different sets of orifices 225, they adjust the device 100 based on the child's size.

Figure 2B:
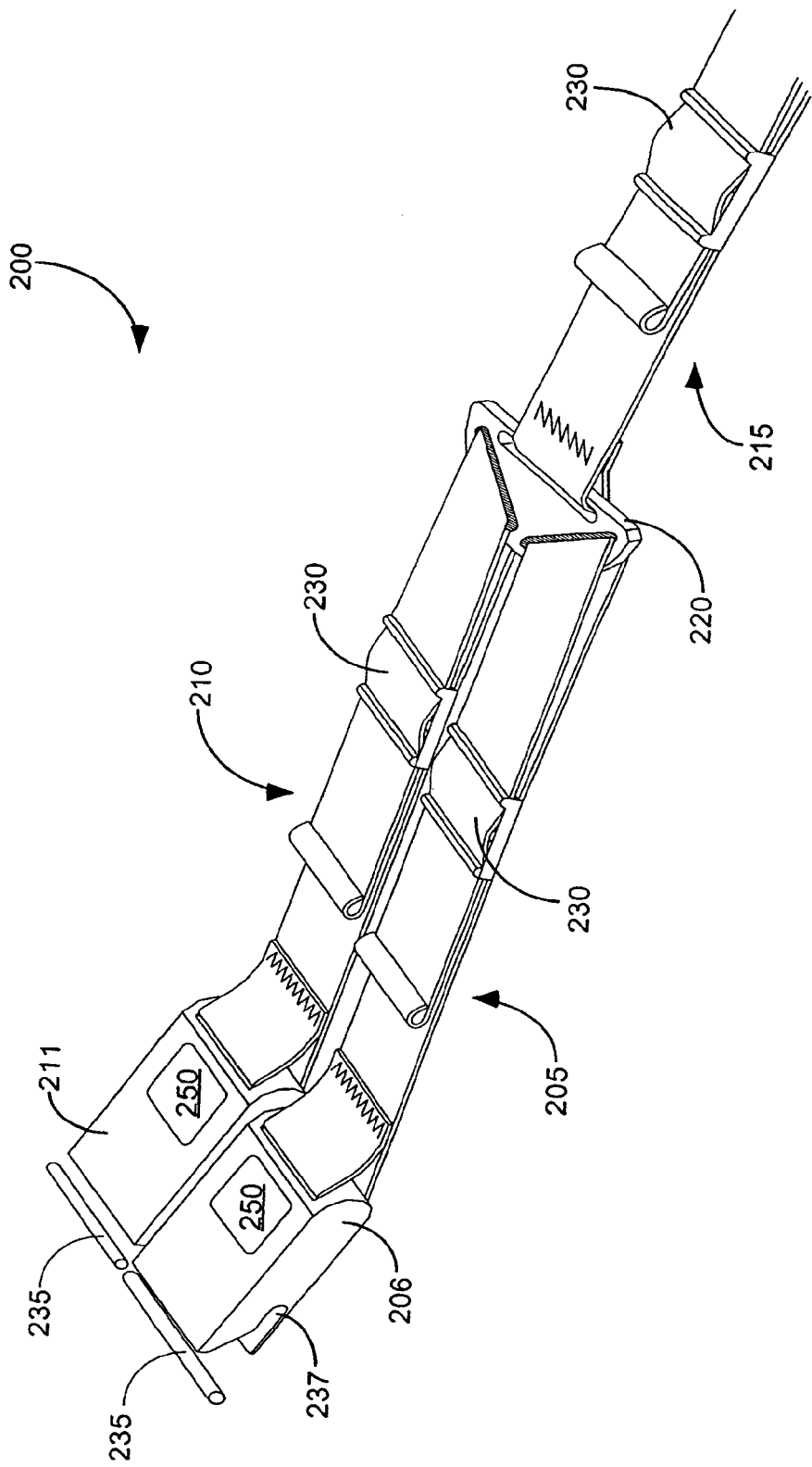
FIG. 2B is a perspective view illustrating the restraining belt assembly of FIG. 2A.

FIG. 2B is a detailed perspective view of the restraining belt assembly 200 that illustrates another length adjustment feature of the device 100. Medical personnel may further accommodate the size of a child using a length adjustment 230. The belts 205, 210, 215 include the length adjustment 230 that varies the length of the corresponding belt. For example, a child may have a small upper body and long legs. In response, medical personnel may shorten the belts 205, 210 and lengthen the belt 215. Using the selection of orifices 225 and the length adjustment 230 medical personnel can effectively confine children in the device 100. Moreover, these features enable size accommodation without removing the child from the device 100.

Figure 2C:
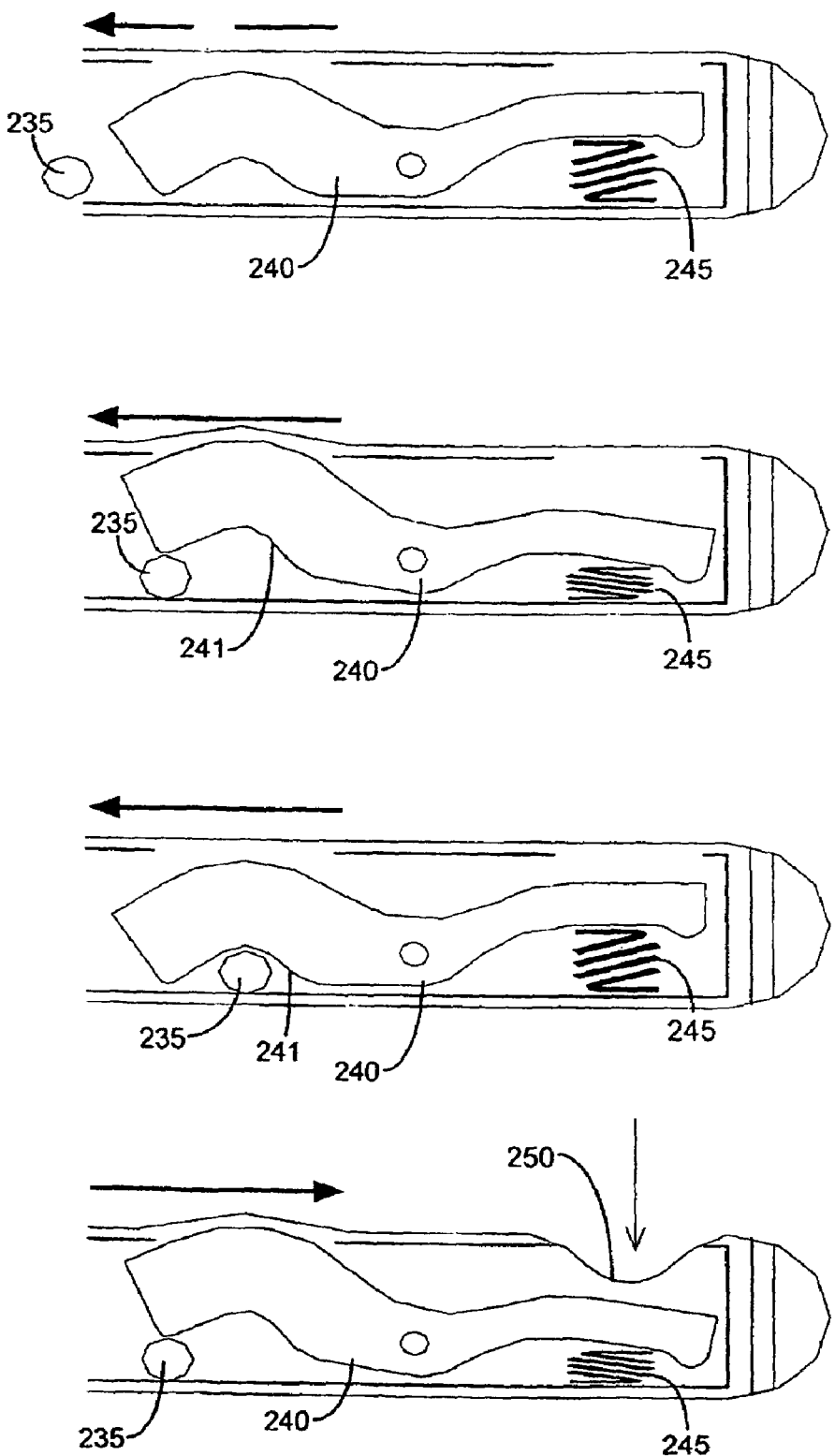
FIG. 2C is a side view of a buckle used with restraining belt assembly of FIG. 2A.

FIGS. 2A, 2B and 2C illustrate the operation of the buckles 206, 211 that secure a child 120 to the device 100. Medical personnel move the buckles 206, 211 toward a plurality of belt anchors 235 centered in the orifices 225. Because buckles 206, 211 contact the anchors 235 and operate identically, the operation of buckle 206 is described for simplicity. As the buckle 206 encounters the anchor 235, a buckle guide 237 directs the anchor 235 towards a locking plate 240 (FIG. 2C). The locking plate 240 pivots in response to contact from the anchor 235. The pivoting of the locking plate 240 creates a spring force by compressing a spring 245. As the anchor 235 contacts a bottom side 241 of the locking plate 240, the spring force releases. As it releases, the locking plate 240 pivots back to its original position. This sequence of actions secures, the restraining belt assembly 200 to the section 110. Consequently, the child is secured to the device 100 for emergency transport of pediatric patients.

To remove a child from the device 100, medical personnel press a release button 250. This creates a spring force by compressing the spring 245 and rotates the locking plate 240. While holding the release button 250, they may pull the buckle 206 away from the anchor 235. Because the locking plate 240 has rotated, the anchor 235 can clear the buckle 206. Thus, pulling away releases the anchor 235 from the buckle 206 and removes the restraint from the child. Since the restraint is detached, medical personnel may remove the child causing the belt 205, 210, 215 to fall aside.

Medical personnel can either secure or release the restraining belt assembly 200 with a single action namely pressing the buckle 206 into engagement with respective actions. The single action of connecting the buckle secures a child and engages the restraining belt assembly 200. The single action of pressing the release button 250 releases a child and disengages the restraining belt assembly 200. Because each buckle of the restraining belt assembly 200 engages or disengages with a single action, medical personnel save time. Hence, they may use the device 100 for emergency transport of pediatric patients with greater efficiency.

Figure 3A:
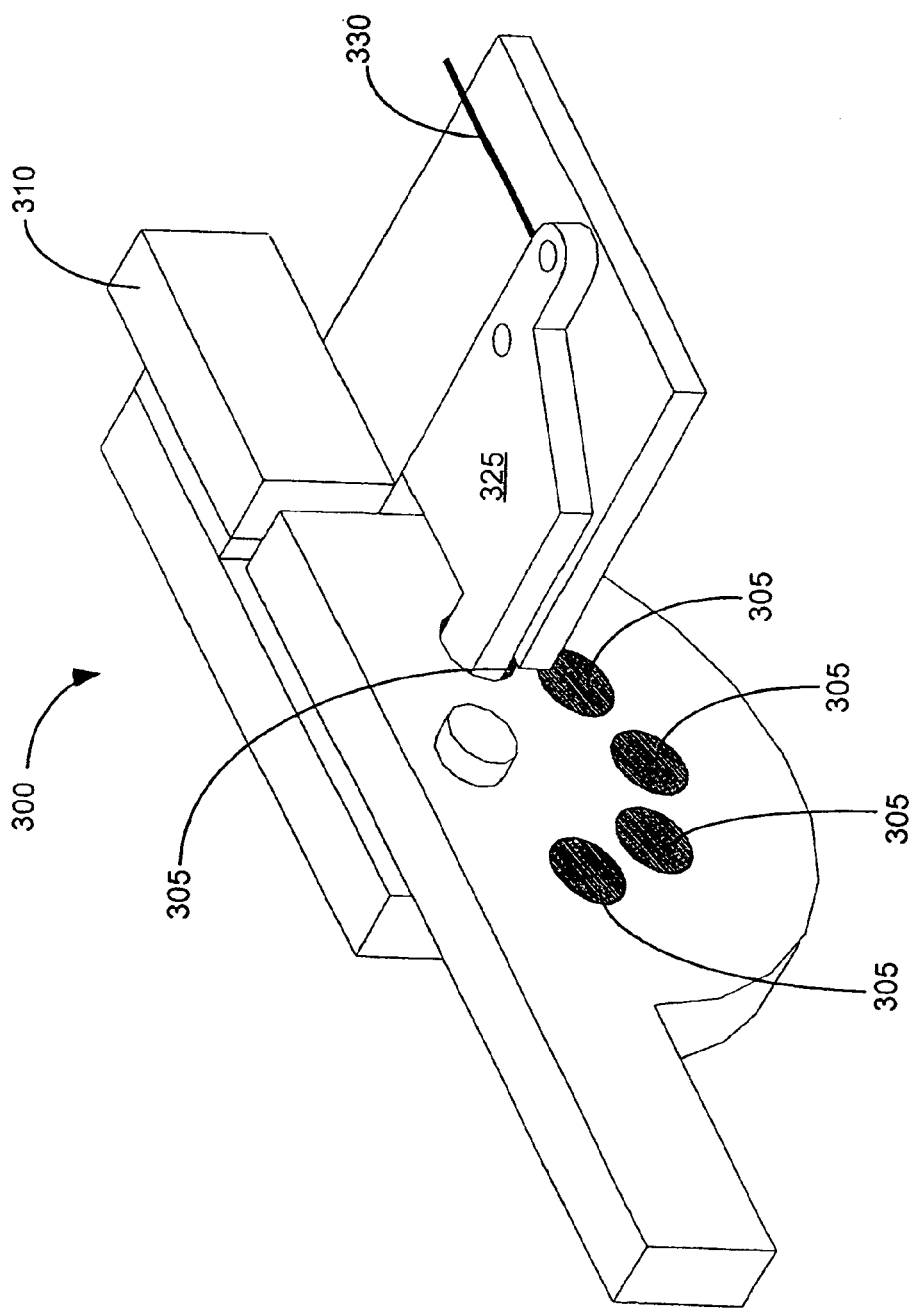
FIG. 3A is a perspective view illustrating a portion of the hinge assembly.

FIG. 3A illustrates a portion of the hinge assembly included in the device 100. This hinge assembly controls the rotation of the section 110 relative to the section 115 and includes a hinge frame 300 and an actuation device. The hinge frame 300 connects to the section 110 by a piece 310 and connects to the section 115 in a similar manner (not shown). The actuation device controls the relative movement between the sections 110, 115 and includes a locking pin 325 and a cable 330. The locking pin 325 selectively engages one of a plurality of orifices 305 in the hinge frame 300 as the cable 330 moves. The actuation device also includes a lever 335 connected to the cable 330 as shown in FIG. 3B.

Figure 3B:
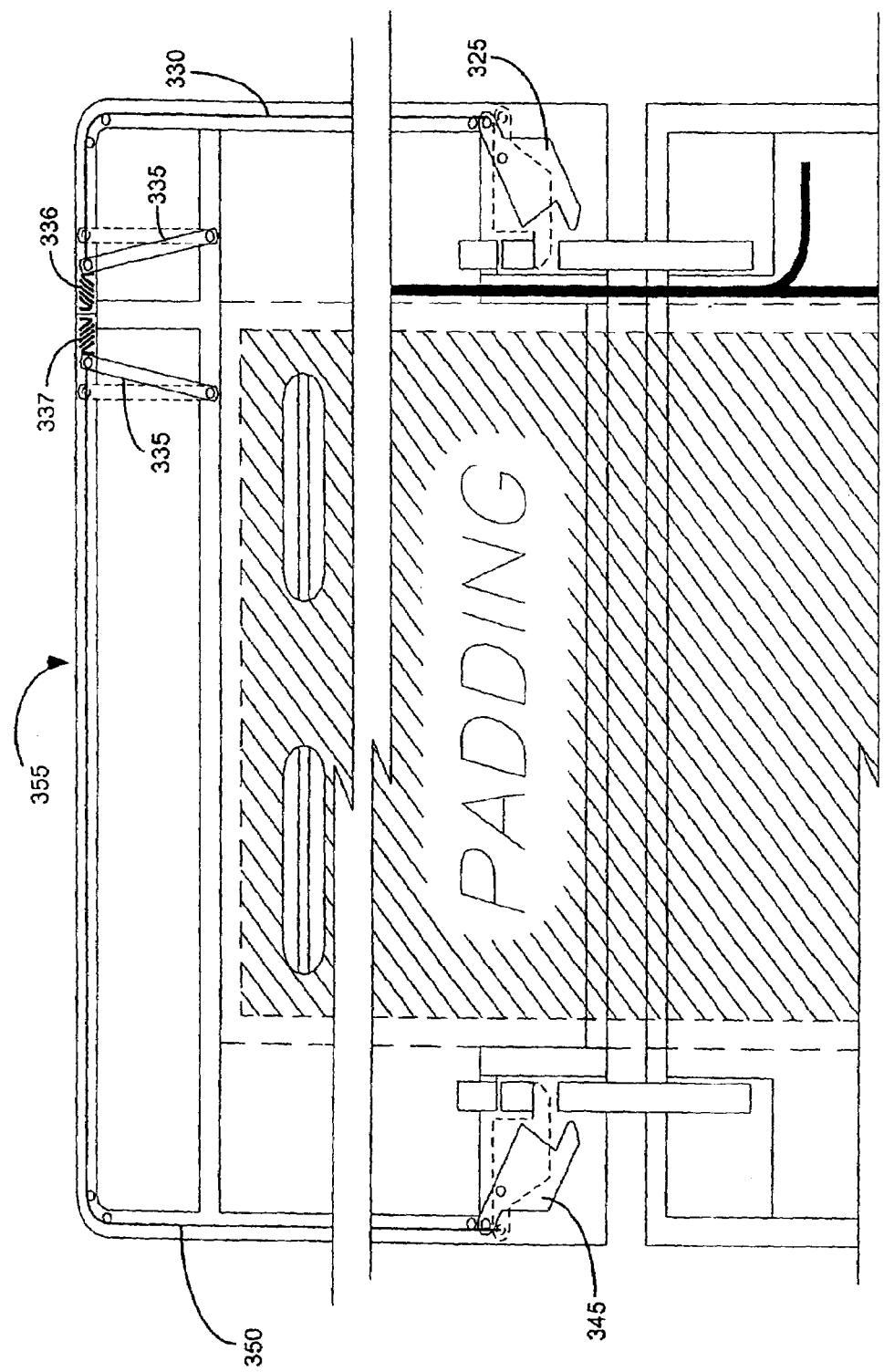
FIG. 3B is a planar view illustrating an actuation device for use with the hinge assembly of FIG. 3A.

FIG. 3B illustrates the operation of the hinge assembly as medical personnel squeeze the lever 335. This action compresses the springs 336, 337 and separates the locking pin 325 from an orifice 305 in the hinge frame 300. While squeezing the lever 335, they may manually rotate the section 110 into a desired position. When desired, a handle 355 aids movement of the section 110 as medical personnel clasp the lever 335. Once the desired position is reached, medical personnel release the lever 335. The release of the springs 336, 337 expands the lever 335. As a result, the locking pin 325 selectively locks in the closest orifice 305 and secures the section 110 in approximately the desired position. It follows that the positions of the orifices 305 dictate the relative angular displacement of the section 110 from the section 115. The orifices 305 may correspond to angular displacements of 0°, 45°, 90°, 135° and 180°. Alternatively, the orifices 305 may correspond to displacements of 0°, 10°, 20°, 30°, and 40°. Hence, both the angular displacements and number of orifices 305 may vary as desired.

Practical implementation of this present invention may demand that it include a second hinge assembly also shown in FIG. 3B. The second hinge assembly could rotate the other side of the section 110. It could include the hinge frame 340, a locking pin 345, a cable 350 and may be used with the lever 335. The hinge frame 340, locking pin 345, and cable 350 function identically to the hinge frame 300, locking pin 325, and cable 330. Because the two hinge assemblies function identically, previous references identify the hinge assembly that includes the frame 300, for simplicity. In addition, both hinge assemblies engage as a single unit with the single action of squeezing the lever 335 and disengages with the single action of releasing the lever 335. Using the hinge assembly reduces the time medical personnel spend positioning the device 100 for emergency transport of pediatric patients. This leads to more efficient operation.

Figure 3D:
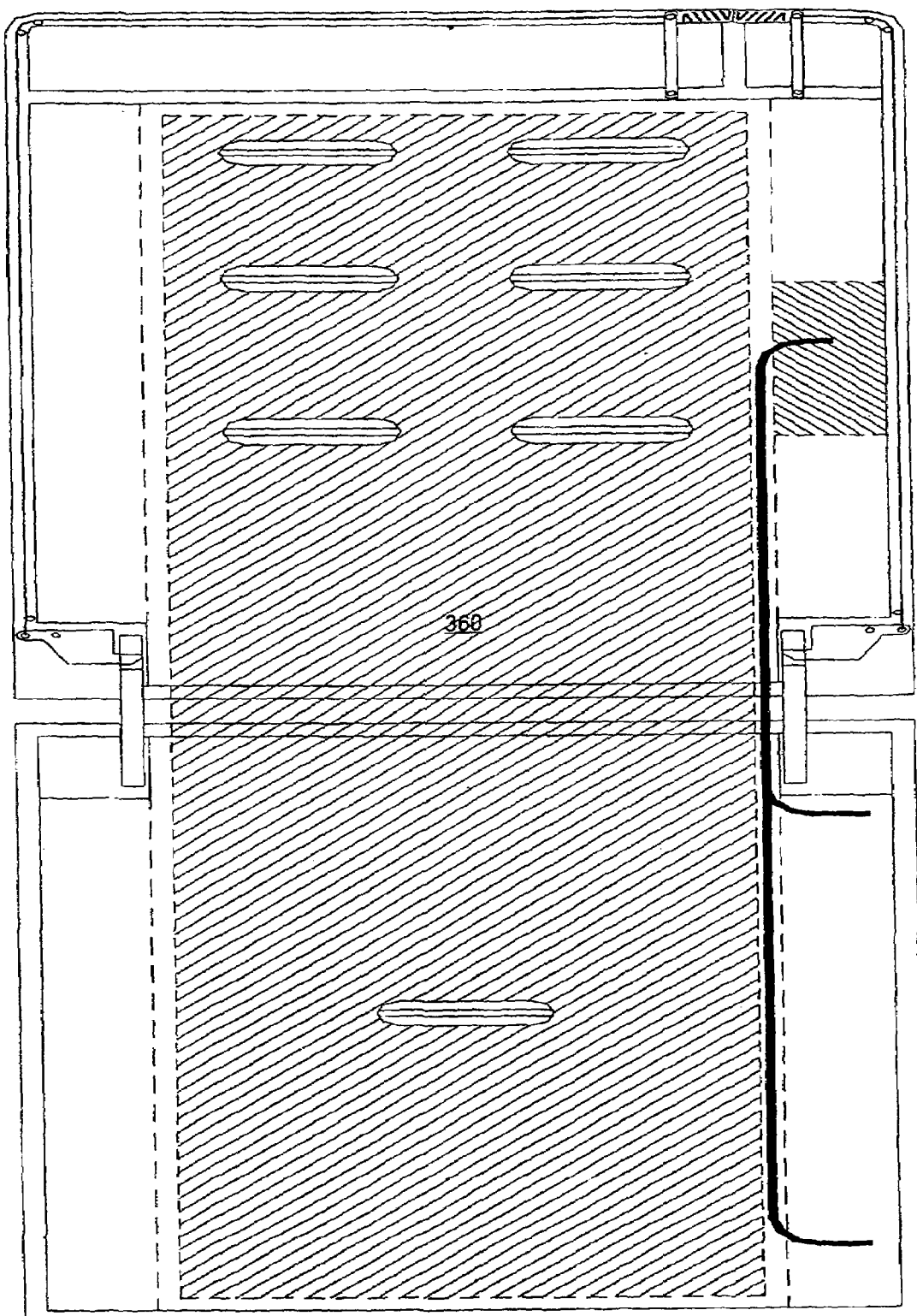
FIG. 3D is a planar view illustrating a pad.

In addition to controlling the rotation of the section 110, select angular displacements may serve particular purposes. FIG. 3C is a side view illustrating the collapsibility feature of the device 100. For an angular displacement of 0°, the section 110 folds on top of the section 115 enabling the device 100 for emergency transport of pediatric patients to be stored easily in a compact environment such as an ambulance. For an angular displacement of 180° of the section 110, the device 100 lies parallel to a stretcher. In this position, medical personnel can administer cardiopulmonary resuscitation (CPR), without removing the child from the restraining device 100. FIG. 3D illustrates a pad 360 that would not impede the administration of CPR if used with the device 100. As described in greater detail hereinafter, the pad 360 may have a corresponding cover that protects the pad 360 from fluids and bacteria transmission. Alternatively, a removable cushion may be used in conjunction with the pad 360 to provide additional comfort.

Figure 4A:
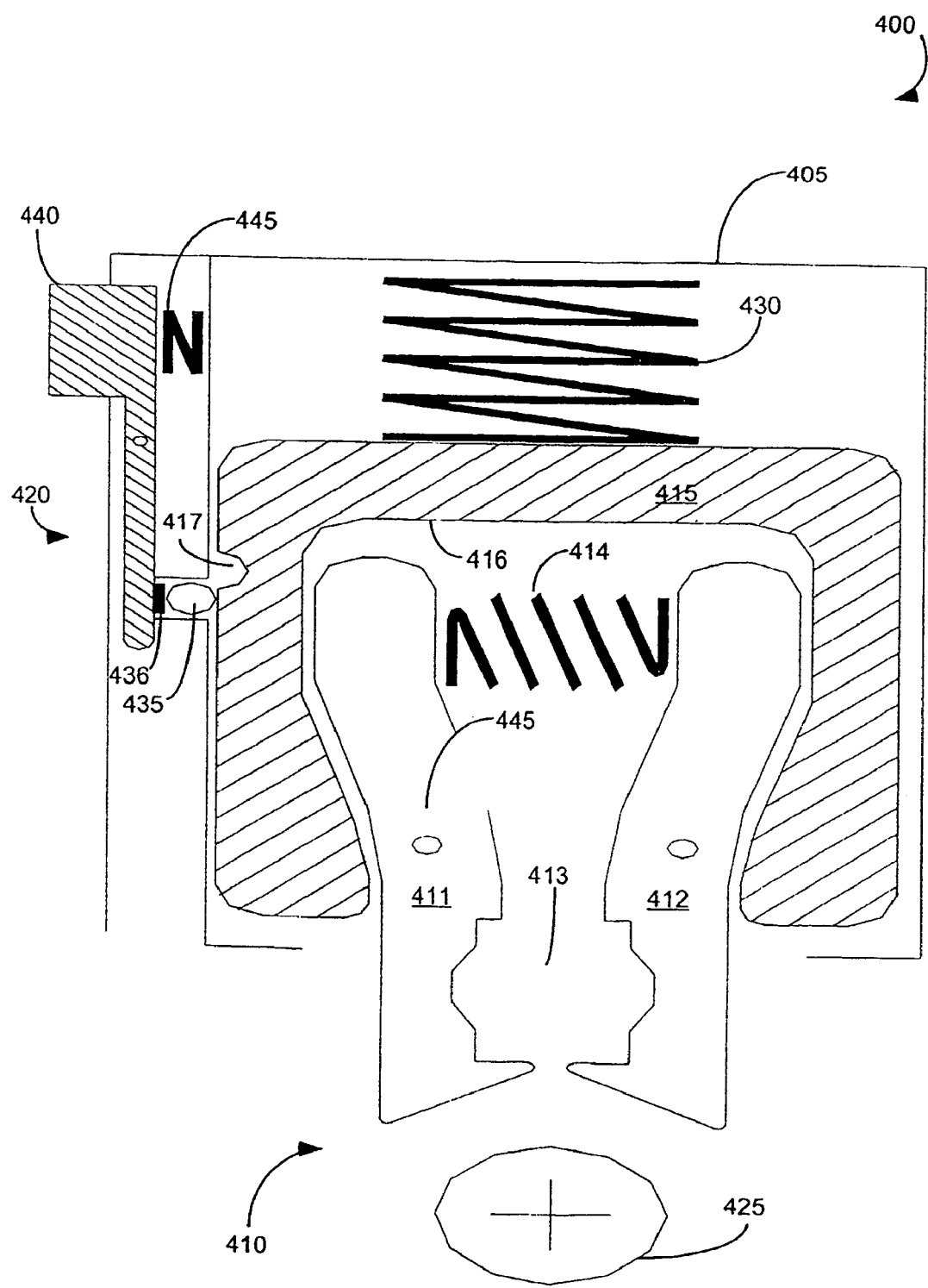
FIG. 4A is a planar view illustrating a clamp.

FIG. 4A illustrates a clamp 400 included in the device for emergency transport of pediatric patients 100. The clamp releasably couples a stretcher to the device 100. The clamp 400 includes a housing member 405, grasping device 410, cam 415, and locking device 420. The grasping device 410 includes fingers 411, 412, groove 413, and spring 414. The locking device 420 includes a locking ball 435, locking ball spring 436, and release 440 having a return-spring 445. The locking ball 435 and locking ball spring 436 form a locking ball detent. The cam 415 surrounds a substantial portion of the grasping device 410. The shape of the inner surface 416 of the cam 415 allows it to be positioned in close proximity to the fingers 411, 412. The locking ball 435 couples to the cam 415 by a groove 417. The cam 415 connects to the housing member 405 through a spring 430.

Figure 4B:
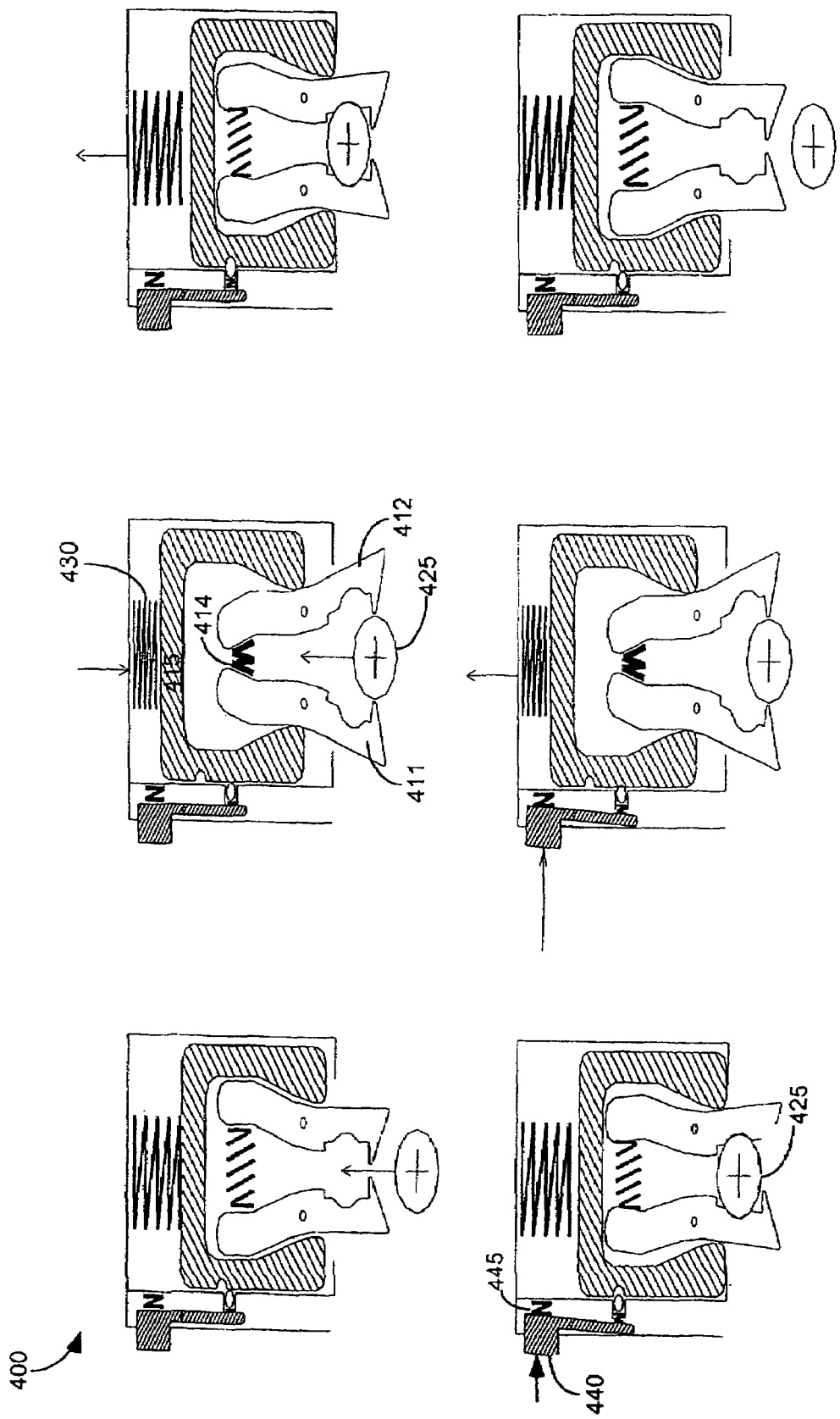
FIG. 4B is a planar view illustrating the operation of the clamp for one type of rail.

FIGS. 4A and 4B together illustrate the operation of the clamp 400. To secure the clamp 400 to a rail 425, an operator may perform the single action of pushing the device 100 with the clamp 400 extended towards the rail 425. As the fingers 411, 412 contact the rail 425, they pivot moving the rail 425 toward the groove 413. As the fingers 411, 412 pivot, they compress the spring 414 and contact the cam 415. In response, the cam 415 moves upward within the housing member 405 and compresses the spring 430. As the rail 425 rests within the groove 413, the spring 414 releases and rotates fingers 411, 412. The spring 430 also releases and moves the cam 415 downward in the housing member 405.

Though the clamp 400 is coupled to the rail, medical personnel may lock it by pulling upward on the device 100 for emergency transport of pediatric patients. This moves the cam 415 further downward in the housing member 405. As the groove 417 of the cam 415 reaches a position adjacent to the locking ball 435, the force from locking spring 436 thrusts the locking ball 435 into the groove 417. Thus, the locking ball 435 secures the cam 415 and the clamp 400 in a locked position. The locked position reduces the probability that the device 100 accidentally releases the rail 425.

After locking the clamp 400, medical personnel may release the rail 425 using the single action of pressing the release 440. Medical personnel press the release 440, that releases the cam 415 as the locking ball 435 rolls toward the now displaced locking ball spring 436. As the device 100 is pulled away from the rail 425, the rotation of the fingers 411, 412 forces the cam 415 to compress the spring 430. Once the rail 425 clears the fingers 411, 412, the force from spring 430 moves the cam 415 back down to its original position.

The locking feature of the clamp 400 may securely attach this present invention 100 to a stretcher 105. Alternatively, the clamp 400 may aid in storing the present invention 100. When used for storage, the device 100 for emergency transport of pediatric patients may secure to a rail on the wall of an ambulance, for example using the clamp 400. In addition, the clamp 400 may also efficiently secure a device to objects of various shapes independent of the device 100.

Figure 4C:
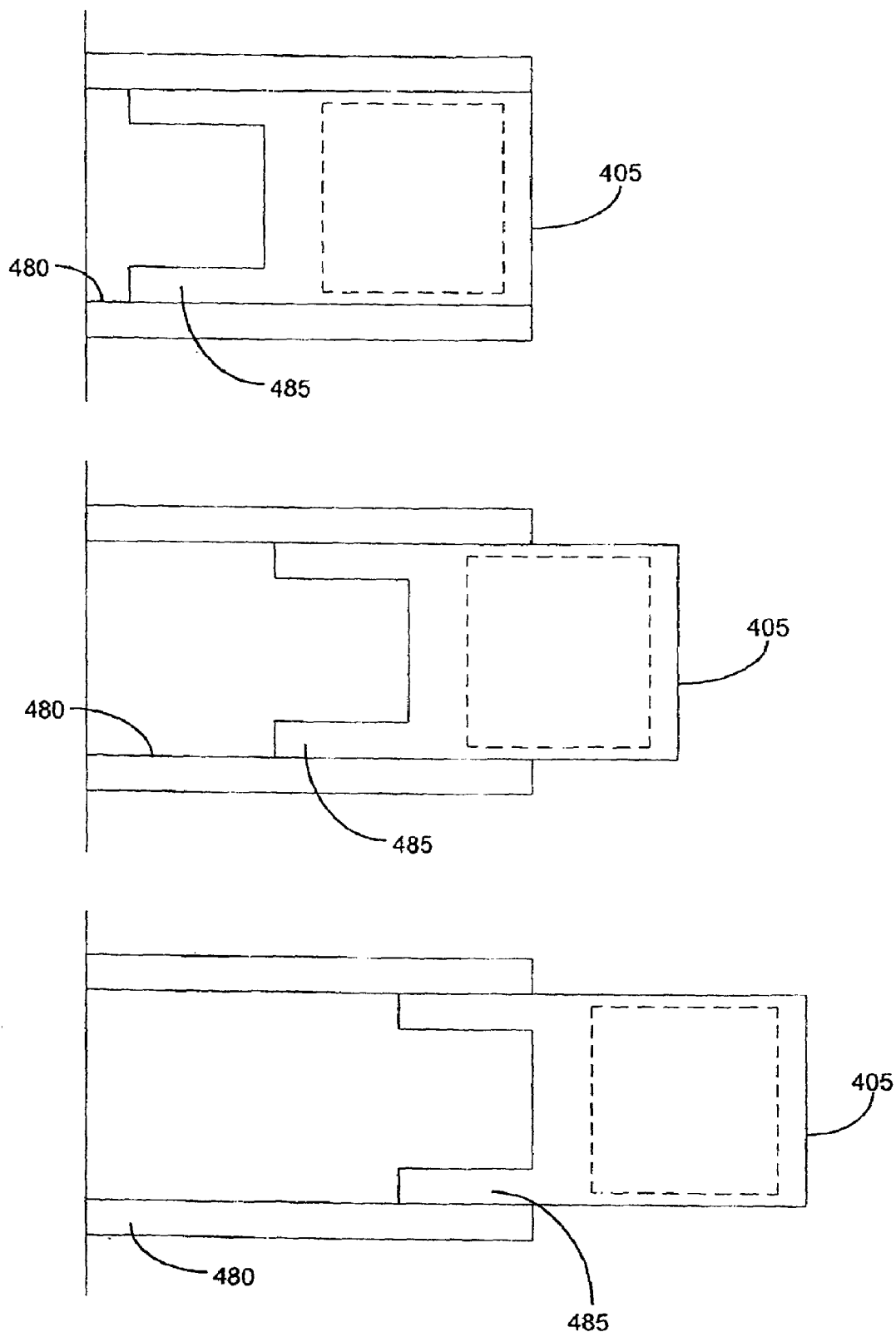
FIG. 4C is a planar view illustrating the width adjustment feature of the clamp of FIG. 4A.

FIG. 4C illustrates the width adjustment feature of the clamp 400. The section 115 includes a frame guide 480 in sliding relation with a clamp guide 485. The clamp guide 485 attaches to the housing member 405. If medical personnel desire connection of the device for emergency transport of pediatric patients 100 to a stretcher of a different size, they vary the displacement between the clamp guide 485 and the frame guide 480. For example, a narrower stretcher may have rails that are closer together. In response, medical personnel push the clamp 400 further into the section 115. This causes the clamp guide 485 to slide along the frame guide 480 until the desired position is reached. A securing device placed between the frame guide 480 and the clamp guide 485 may lock the frame guide and clamp guide at pre-selected rail widths. The securing device may be a locking ball detent, locking pin, or an Allen wrench with corresponding set screw.

FIG. 4D illustrates the adaptability of the clamp 400 to a circular rail 425 and a rectangular rail 499. Medical personnel may utilize this feature by using this present invention 100 with a stretcher. For example, some medical personnel may work for an ambulance company that utilizes two types of stretchers—one with a circular rail and one with a rectangular rail. In an emergency that requires a child transport, the medical personnel in an ambulance with a circular rail 425 would not spend additional time returning to the station before responding to a call in order to pick up a stretcher with a rectangular rail 499 to accommodate the device for emergency transport of pediatric patients. The reverse situation is also the same. The device 100 adapts to both types of rails. Moreover, the clamp 400 may adapt to other rail shapes, such as triangular by appropriately modifying the groove 413. Hence, the universal adaptability of the clamp increases the operating ability of the device 100.

Figure 5:
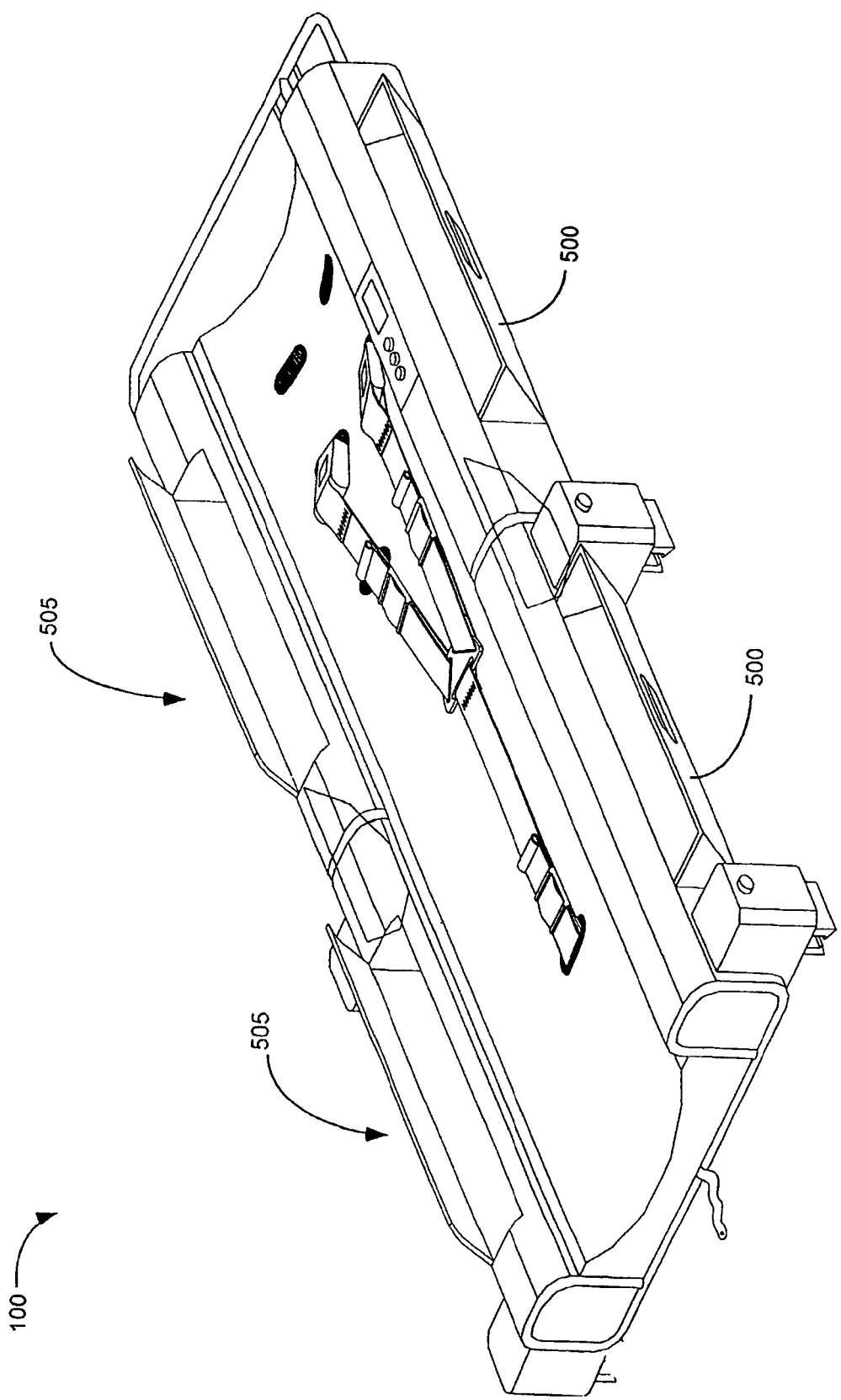
FIG. 5 is a perspective view illustrating storage devices.

As illustrated in FIG. 5, this present invention 100 may also include the storage devices 500, 505. The position of the storage devices 500 corresponds to the side of a stretcher that secures to the ambulance. For example, a stretcher that secures to the right side of an ambulance could also include storage devices 500 on the left side. The storage devices 505 may be on either side of the restraining device 100. The storage devices 500, 505 may contain devices specifically designed to treat pediatric patients, such as pediatric needles or equipment needed to intubate a child.

FIG. 6 illustrates additional features of the device for emergency transport of pediatric patients 100. The device 100 may include a data acquisition device (DAD) 600 as illustrated in FIG. 6. It may be a commercially available device modified to measure an individual's vital signs or weight. The wiring for the DAD 600 may couple to the clamp 400 through a device that converts stress measurements into electrical signals. For example, this device would convert the stress applied to the clamp due to the weight of the child to a number displayed on the DAD 600. Medical personnel could read this number. By knowing the patient's vital signs or weight as measured by the DAD 600, medical personnel may more effectively treat the patient, administering more accurate doses of medication, etc.

Also illustrated in FIG. 6, medical personnel may use a closure strap 605 when the device 100 is collapsed as previously described in relation to FIG. 3C. As mentioned above, the hinge assembly, more specifically the locking pin 325, secures the restraining device in the collapsed position. Yet, medical personnel may visibly indicate the collapsed position using the strap 605. The strap 605 may consist of leather and attach to the section 115, 110 through stitching and a snap, respectively.

Figure 7A:
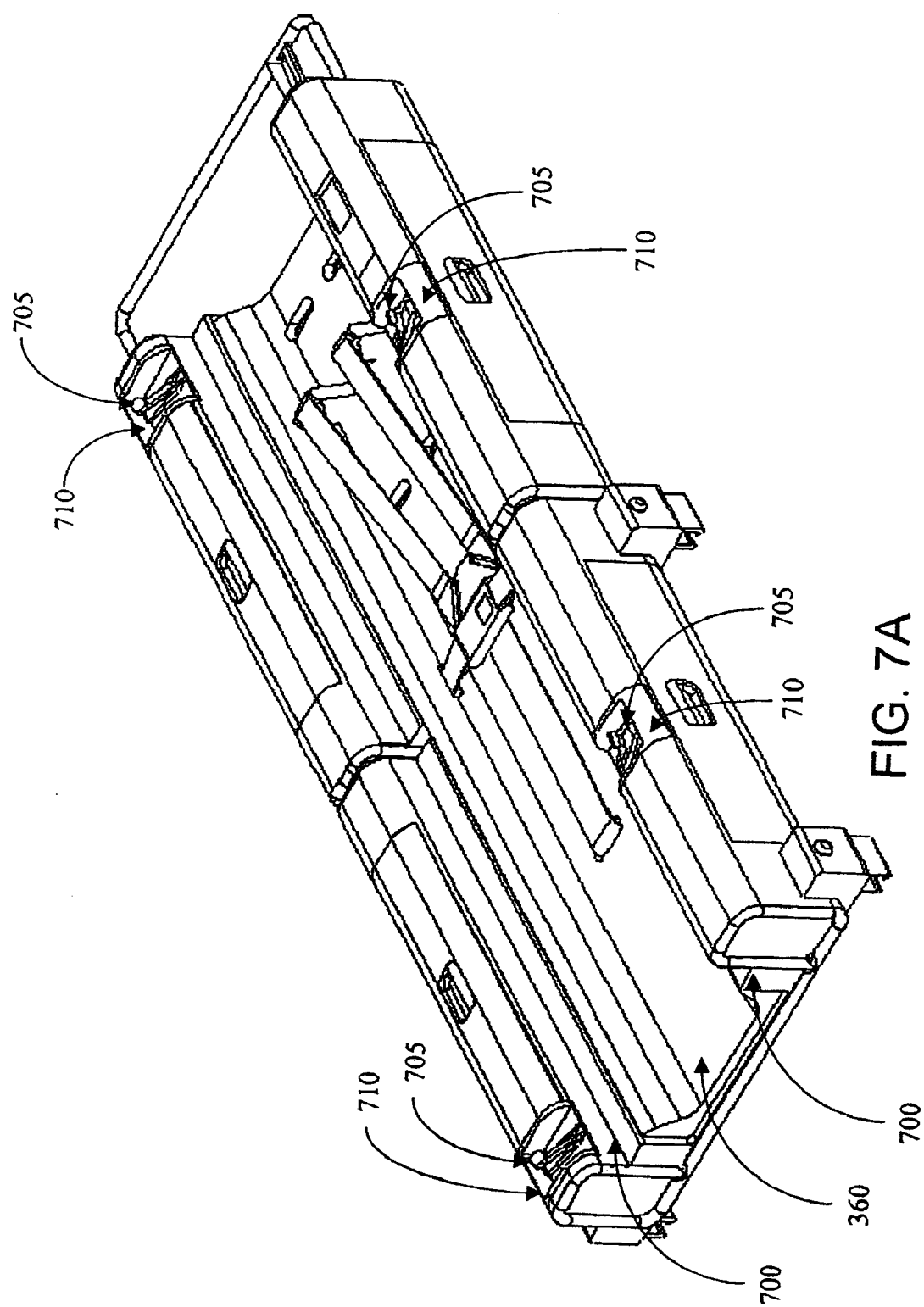
FIG. 7A is a perspective view illustrating one method for modifying the device of FIG. 1 further to allow the use of a conventional backboard therewith.
Figure 7B:
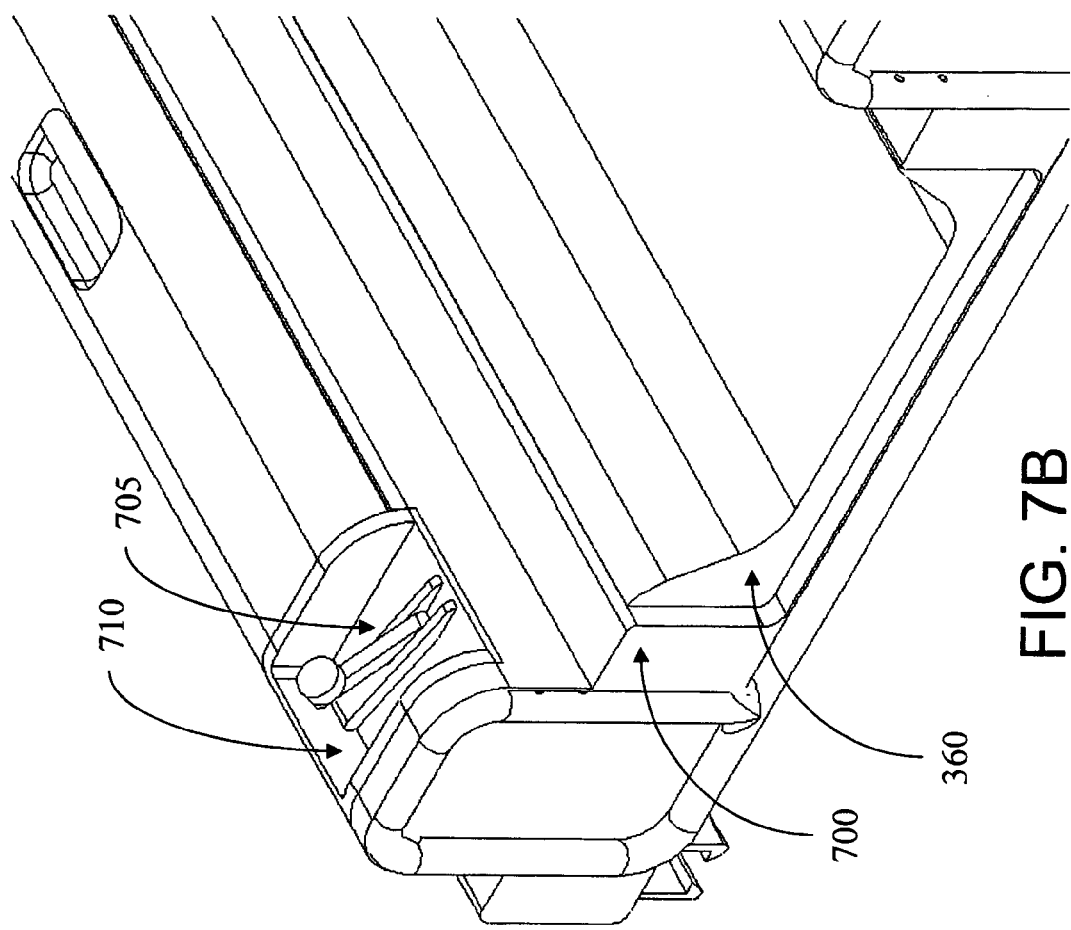
FIG. 7B is a perspective view illustrating a clamp to hold the backboard according to FIG. 7A.
Figure 7C:
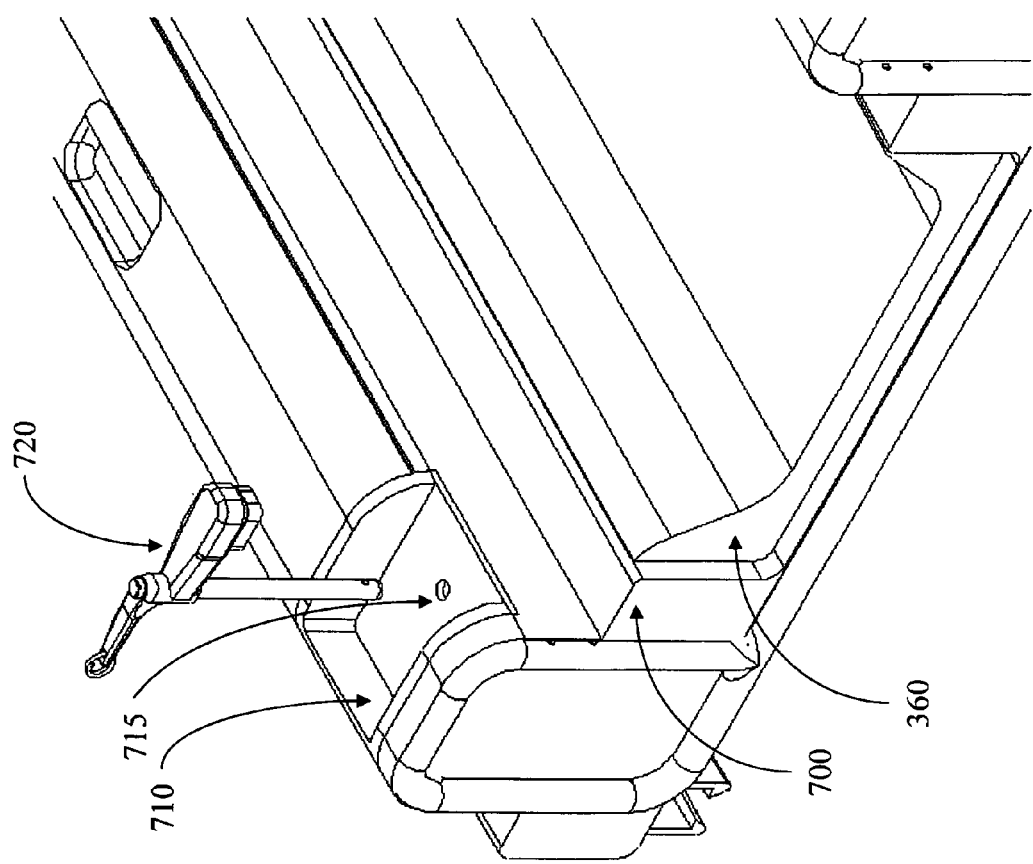
FIG. 7C is a perspective view illustrating a slide in pin suitable for securing a conventional backboard to an emergency transport device of the present invention.

FIGS. 7A-7C together illustrate a further embodiment of the device 100 for emergency transport of pediatric patients to allow the placement of a backboard (not shown) on a ledge within the device. Each side of the device frame preferably includes a ledge 700 that extends towards the interior of the device just above the level of the pad 360 located in the center of the device. The backboard is adapted to rest on these ledges 700 covering the central padded portion 360 of the device 100. Each side of the frame includes one or more small compartments that have been cut into the raised portion of the frame on both sides of the device 100 to serve as housings 710 for the clamp mechanisms 705 or 720 that secure the backboard to the device 100. The clamping mechanism utilized may be cantilever clamps 705, as illustrated, or another such locking mechanism such as a slide in pin 720 locking pin, or the like to secure the backboard rigidly into place. These clamps 705 or other such locking mechanisms (e.g., slide in pin 720 which inserts into slide in pin hole 715), when not in use, are configured to lock or store into place in their housings 710 out of the way of the central padded portion 360 of the device 100.

Figure 8A:
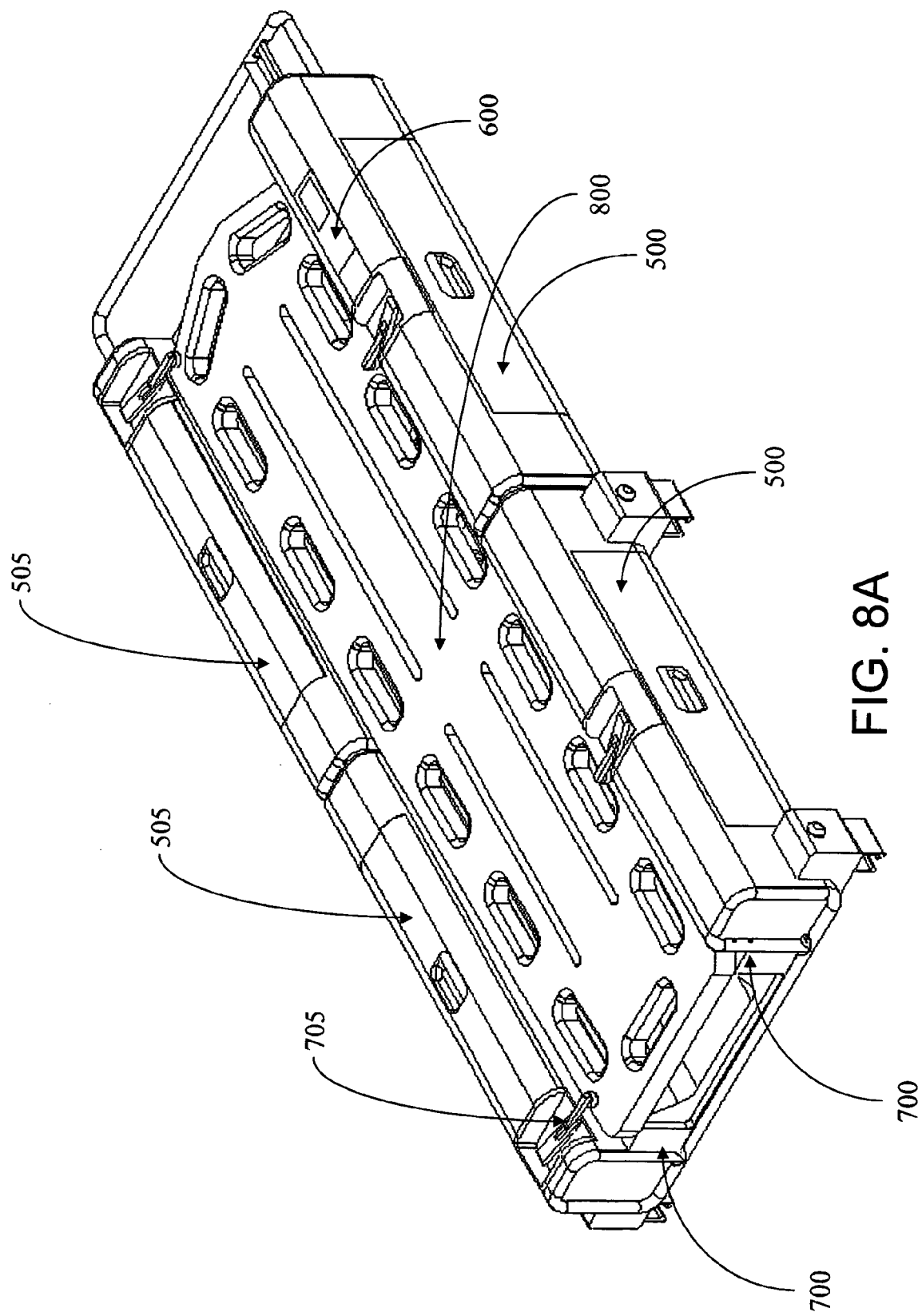
FIG. 8A is another perspective view illustrating a backboard clamped into the device of the present invention using the method illustrated in FIG. 7A.
Figure 8B:
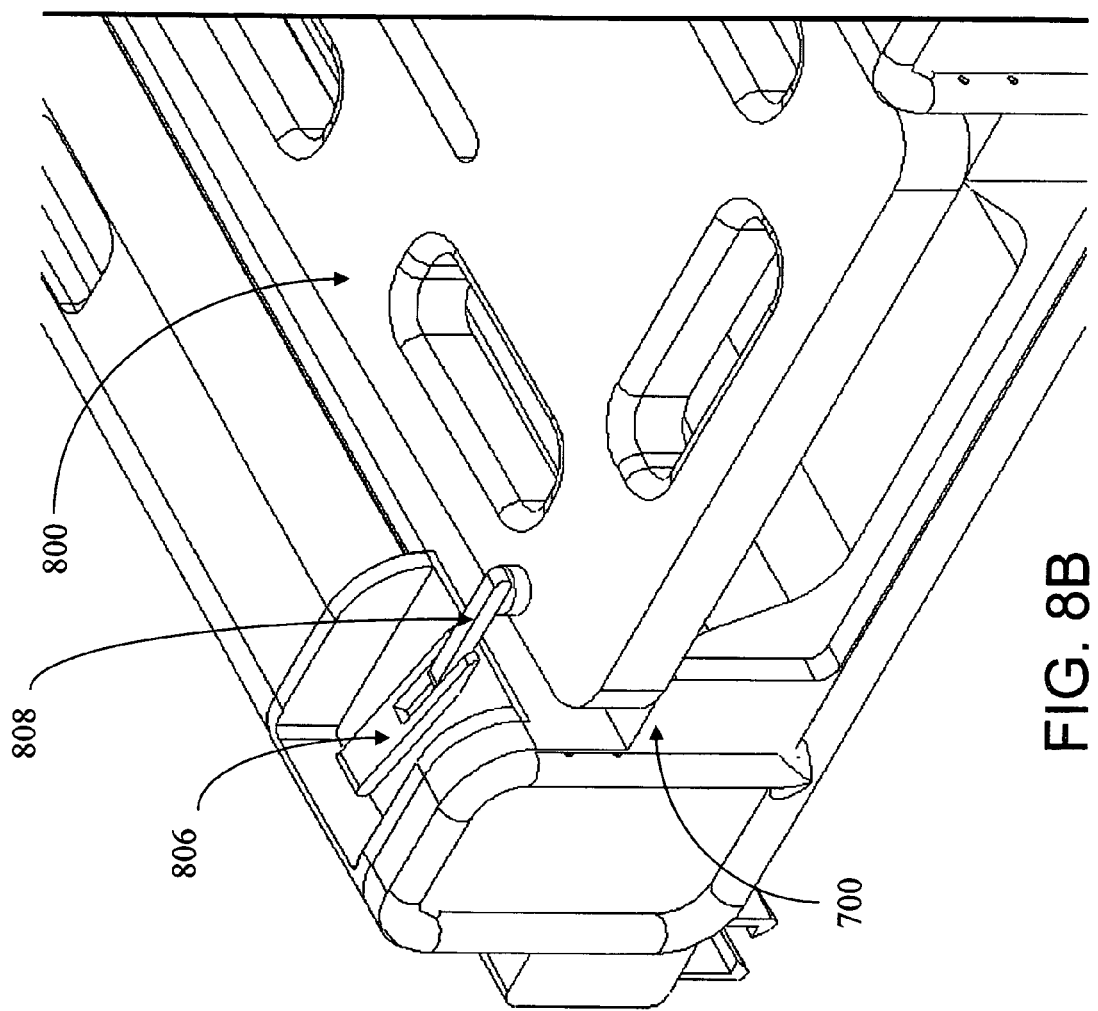
FIG. 8B is a perspective view illustrating a clamp to hold the backboard according to FIG. 8A.
Figure 8C:
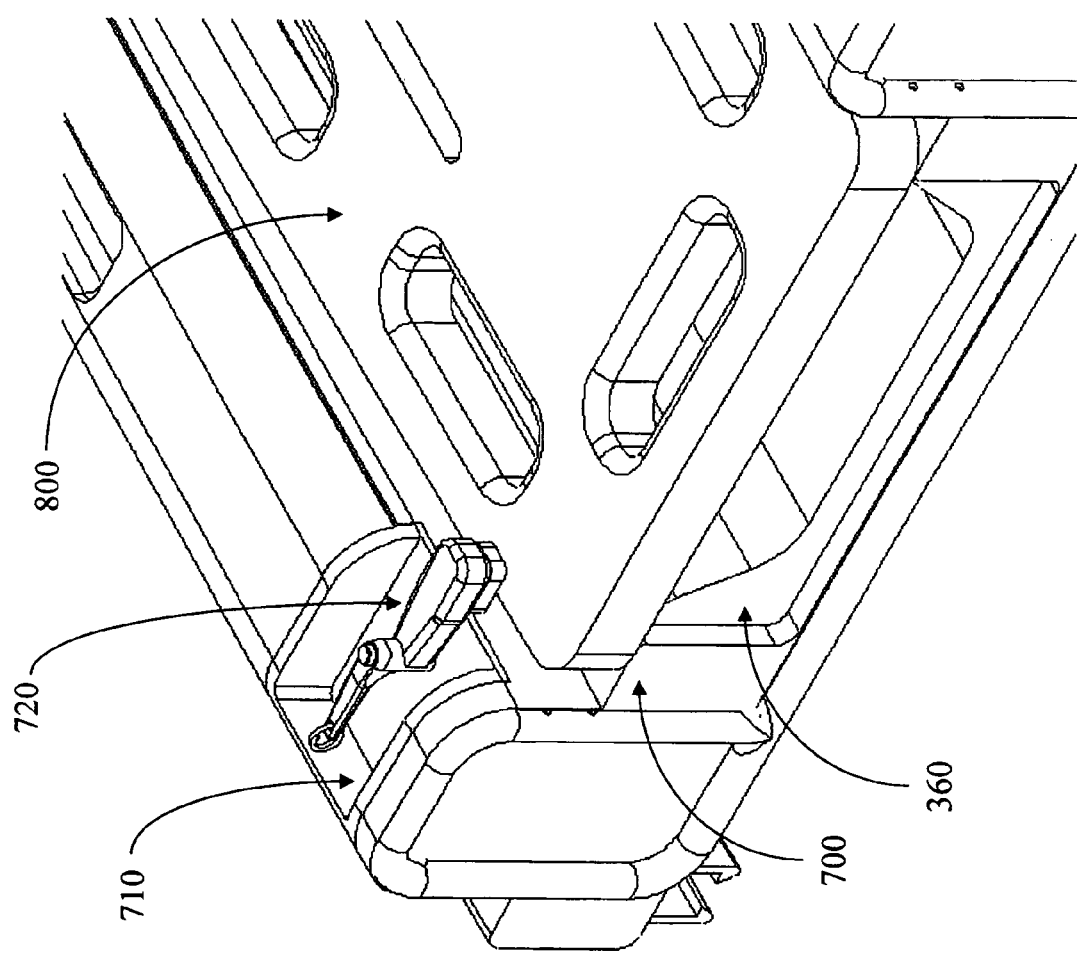
FIG. 8C is a perspective view illustrating a slide in pin securing a conventional backboard to an emergency transport device of the present invention.

FIGS. 8A-8C together illustrate a conventional backboard or conventional pediatric backboard 800 clamped into place on the device 100, as illustrated in FIGS. 7A-7C. A medical technician may immobilize a child on a commercially available off the shelf pediatric backboard 800 using currently acceptable medical practices. They may then place the backboard onto the ledges 700 within the central portion of the device 100. When using a cantilever clamp 705 as the clamping mechanism, the medical technician would start with the clamp 705 in open position residing entirely in its housing 710 as illustrated in FIG. 7B. Referring to FIG. 8B, the central portion of the clamp 808 would be rotated in a clockwise fashion to rest on top of the backboard 800. Pushing downward on the outer portion of the clamp 806 locks the entire clamp in place and secures the backboard 800 to the ledge 700 as illustrated in FIG. 8A. This is a two-step locking mechanism and as such can be accomplished within seconds. When using a slide in pin 720 as the clamping mechanism, the medical technician would start with the slide in pin 720 removed from slide in pin hole 715 as illustrated in FIG. 7C. Referring to FIG. 8C, the slide in pin 720 would be inserted into slide in pin hole 715 so as to rest on top of the backboard 800.

Although a pediatric patient immobilized on a backboard 800 may be secured directly to a stretcher in conventional manner, securing the pediatric patient within the device 100 allows the technician full access to pediatric medical supplies located within the device's storage compartments 500, 505, as well as full access to the device's data acquisition device 600 to obtain accurate information about the child's vital signs en-route. Upon arriving at the destination, the medical technician may choose to unlock the backboard 800 from the device 100 and transfer the child to a stretcher at the facility, so that they may return to active service. To unlock the backboard 800, the medical technician simply pulls up on the outer portion of the clamp 806, which releases the inner portion of the clamp 808 and as a result disengages the locking mechanism securing the backboard 800. The backboard will still be lying on the ledges 700 of the device 100. The technician then lifts the patient still immobilized on the backboard 800 and transfers them as a unit to the waiting stretcher.

Figure 9:
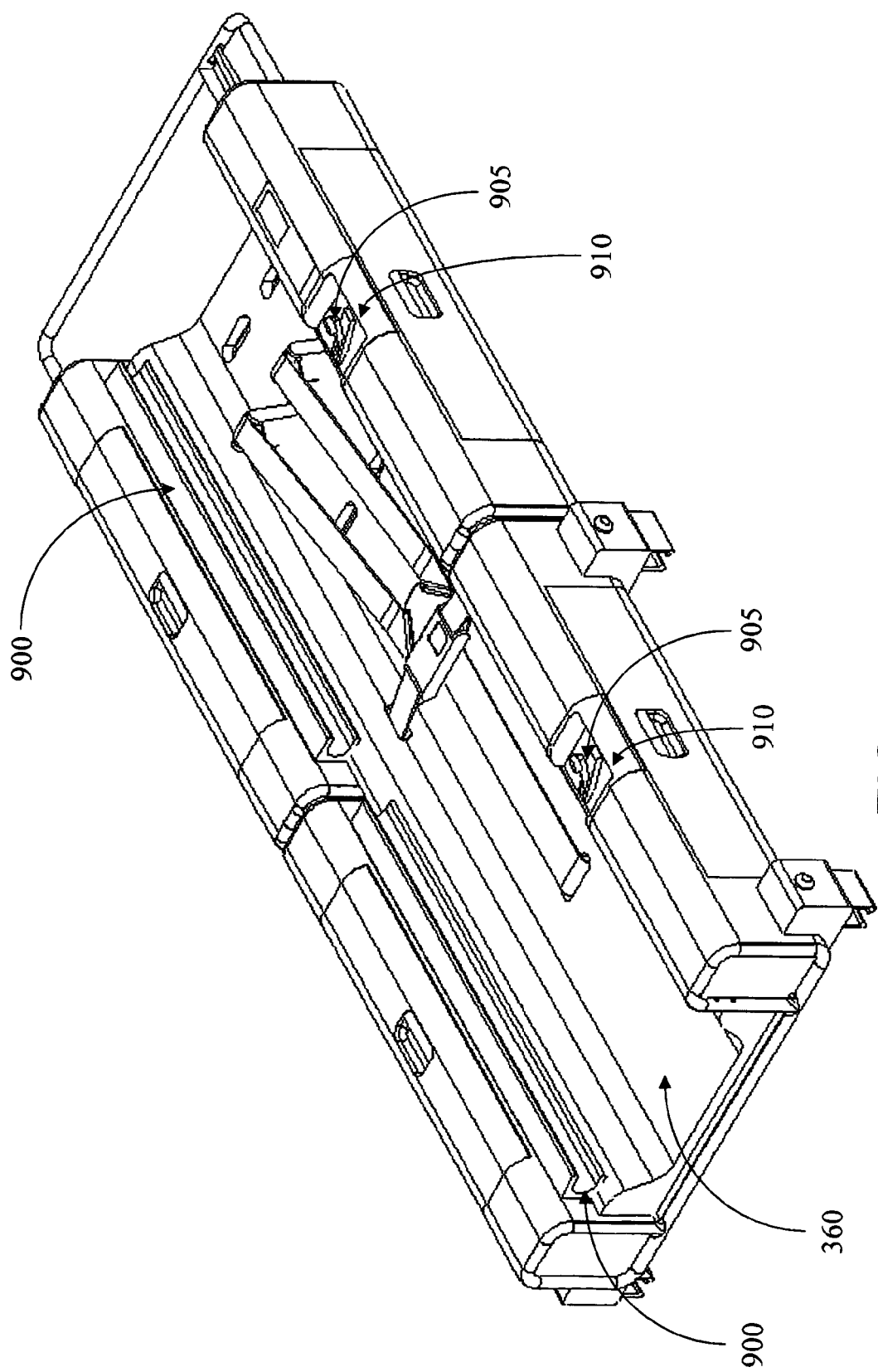
FIG. 9 is a perspective view illustrating an alternative method for modifying the device of the present invention.
Figure 10A:
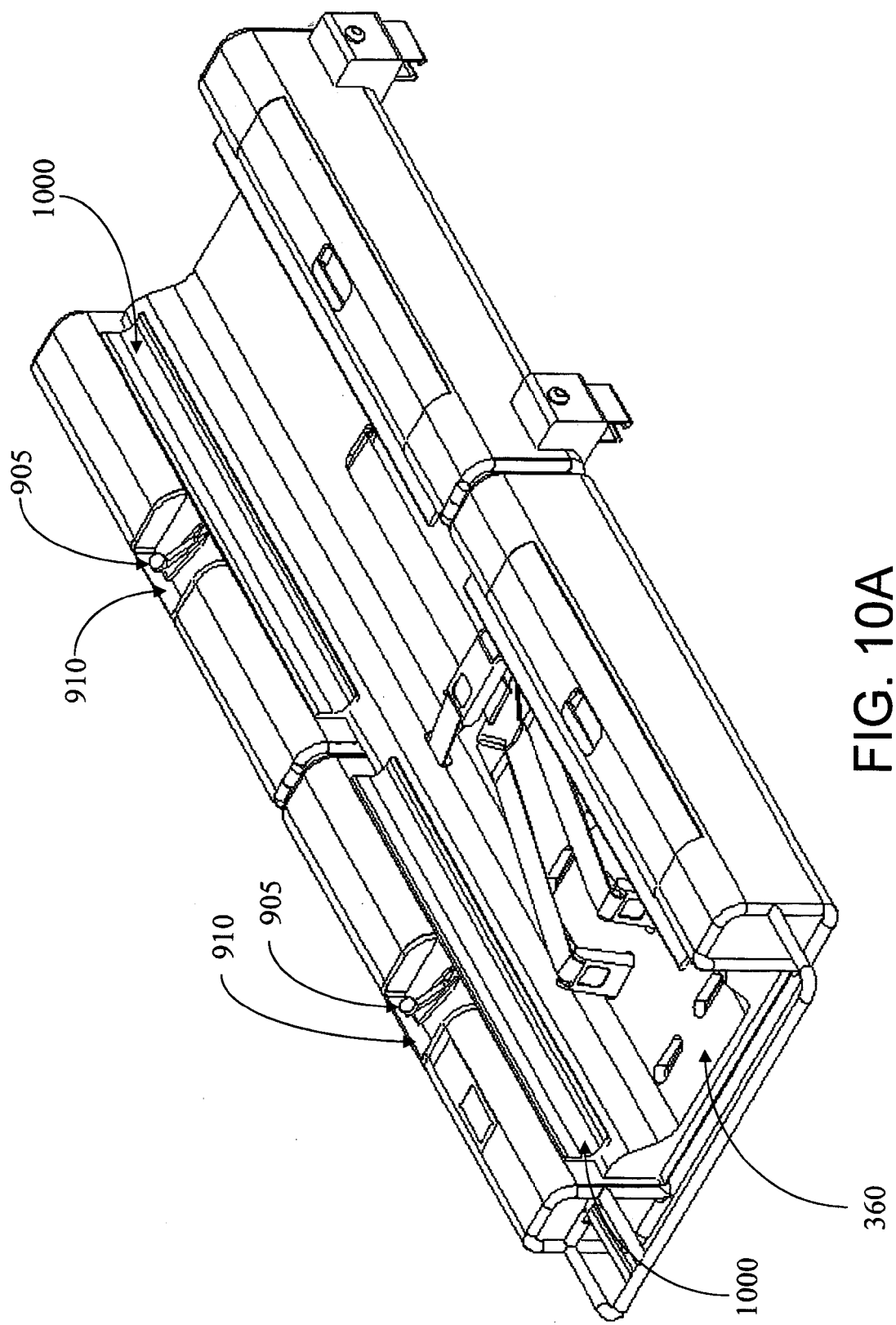
FIG. 10A is another perspective view of the device of the present invention using the alternative method illustrated in FIG. 9.
Figure 10B:
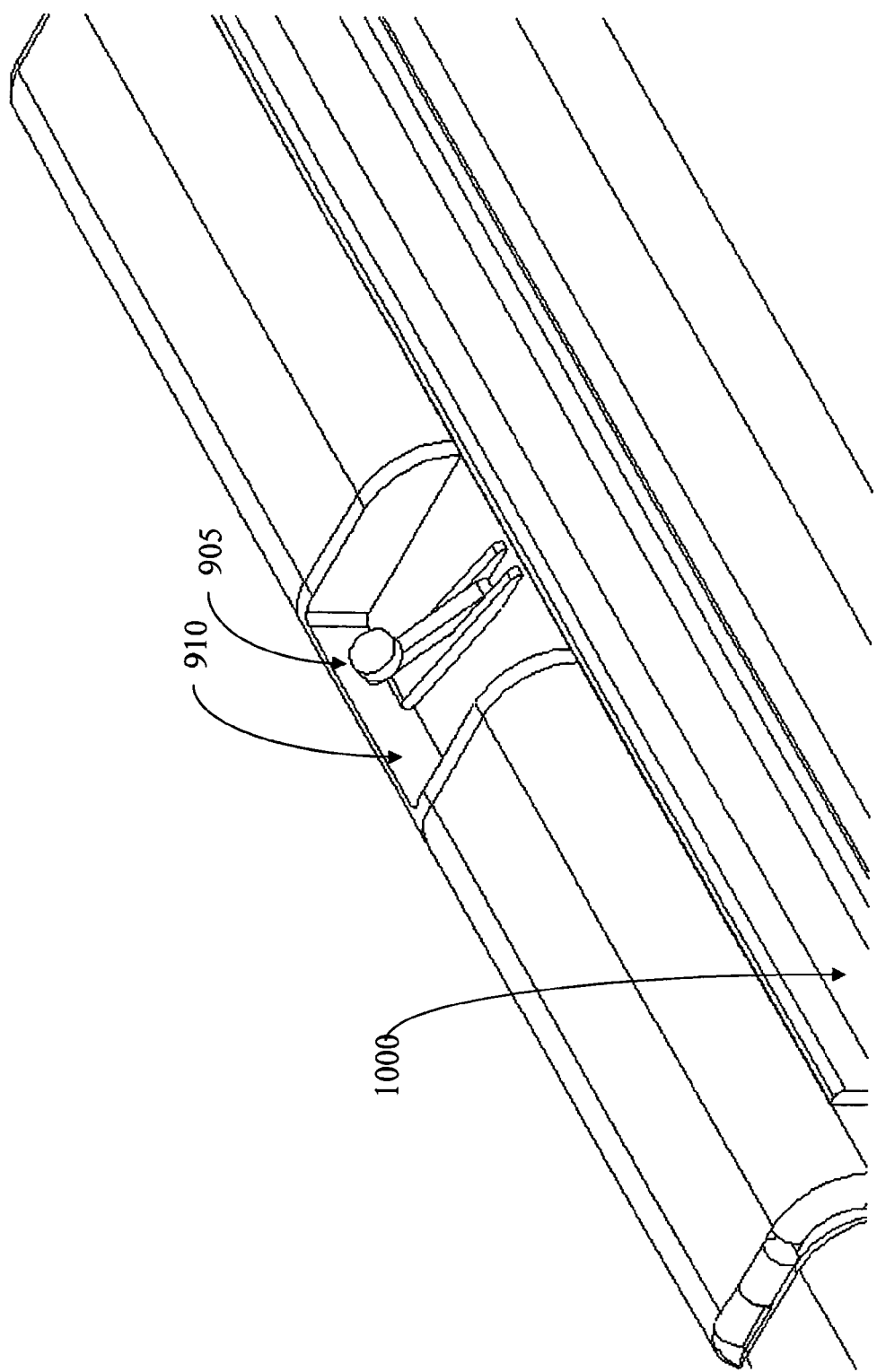
FIG. 10B is a perspective view illustrating a clamp to hold the backboard according to FIG. 10A.

FIGS. 9, 10A, and 10B illustrate an alternative method for modifying the device 100 to receive a conventional backboard or conventional pediatric backboard (not shown). Utilizing this alternative method, one or more channels 900 are affixed to or defined within one side of the frame, and one or more ledges 1000 are added to the opposite side of the frame. The channel is intended to secure the backboard on the channel side of the device 100 without requiring an additional latching mechanism, therefore, clamp mechanisms 905 and clamp housings 910 may only be required on the side of the frame utilizing a ledge 1000.

Figure 11:
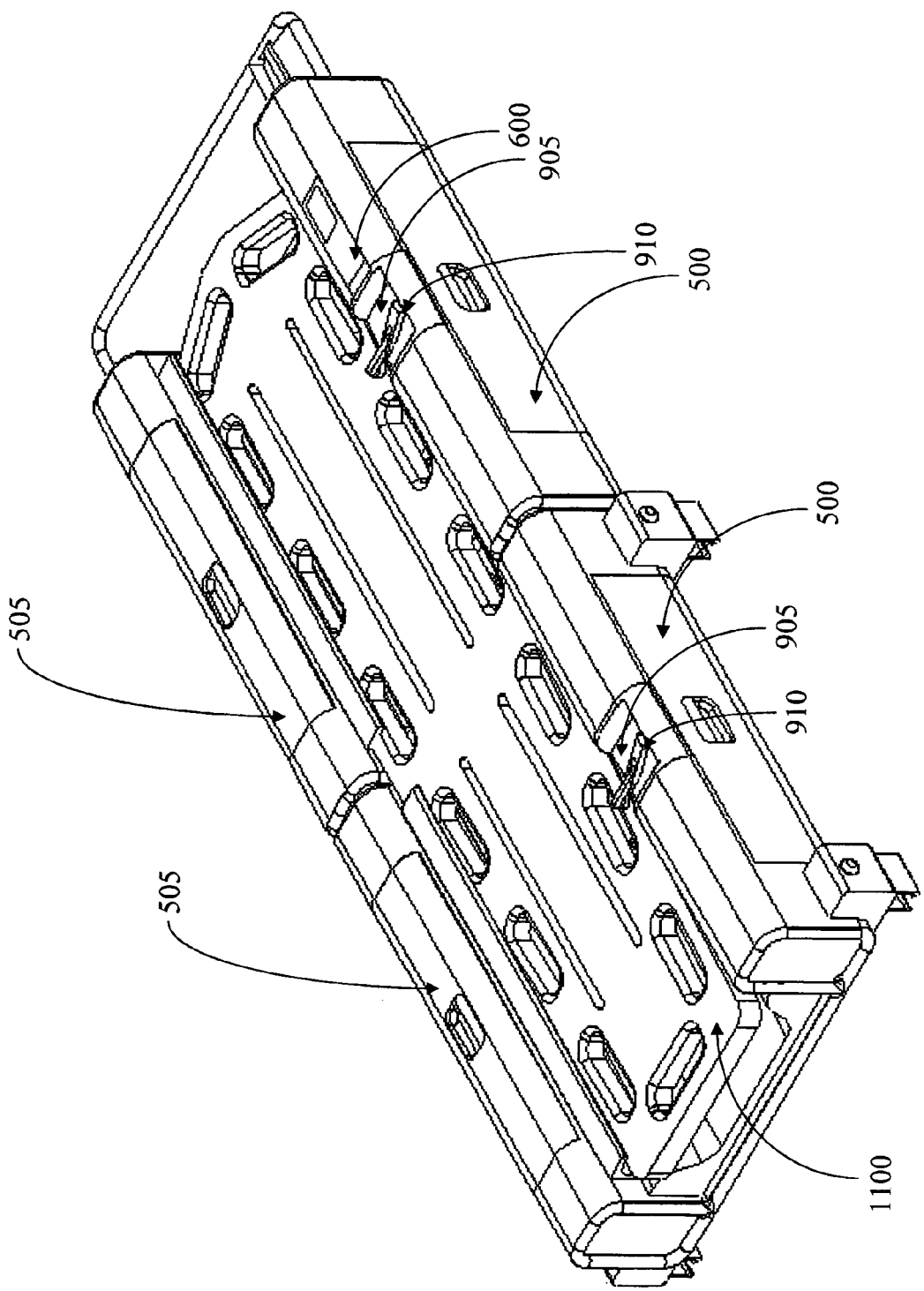
FIG. 11 is a perspective view illustrating a backboard clamped into the device of the present invention using the method illustrated in FIG. 9.

FIG. 11 illustrates a conventional adult or pediatric backboard 1100 locked into place in the device 100. To secure a pediatric patient that has been immobilized on the backboard 1100, the medical technician slides one side of the backboard into the channel and rests the opposite side of the backboard on top of the ledge on the opposite side of the device. The clamping mechanism, seen at rest in FIG. 10B, functions exactly as described previously in association with FIGS. 9, 10a and 10b. To release the backboard 1100 from the device 100, the clamping mechanism 905 is released, as previously described, and returned to rest in its housing 910. The technician lifts one side of the board 1100 slightly off the ledge 1000 and gently slides the other side of the board 1100 out of the channel 900. The child may then be transferred to a waiting stretcher while still strapped to the backboard 1100.

Figure 12:
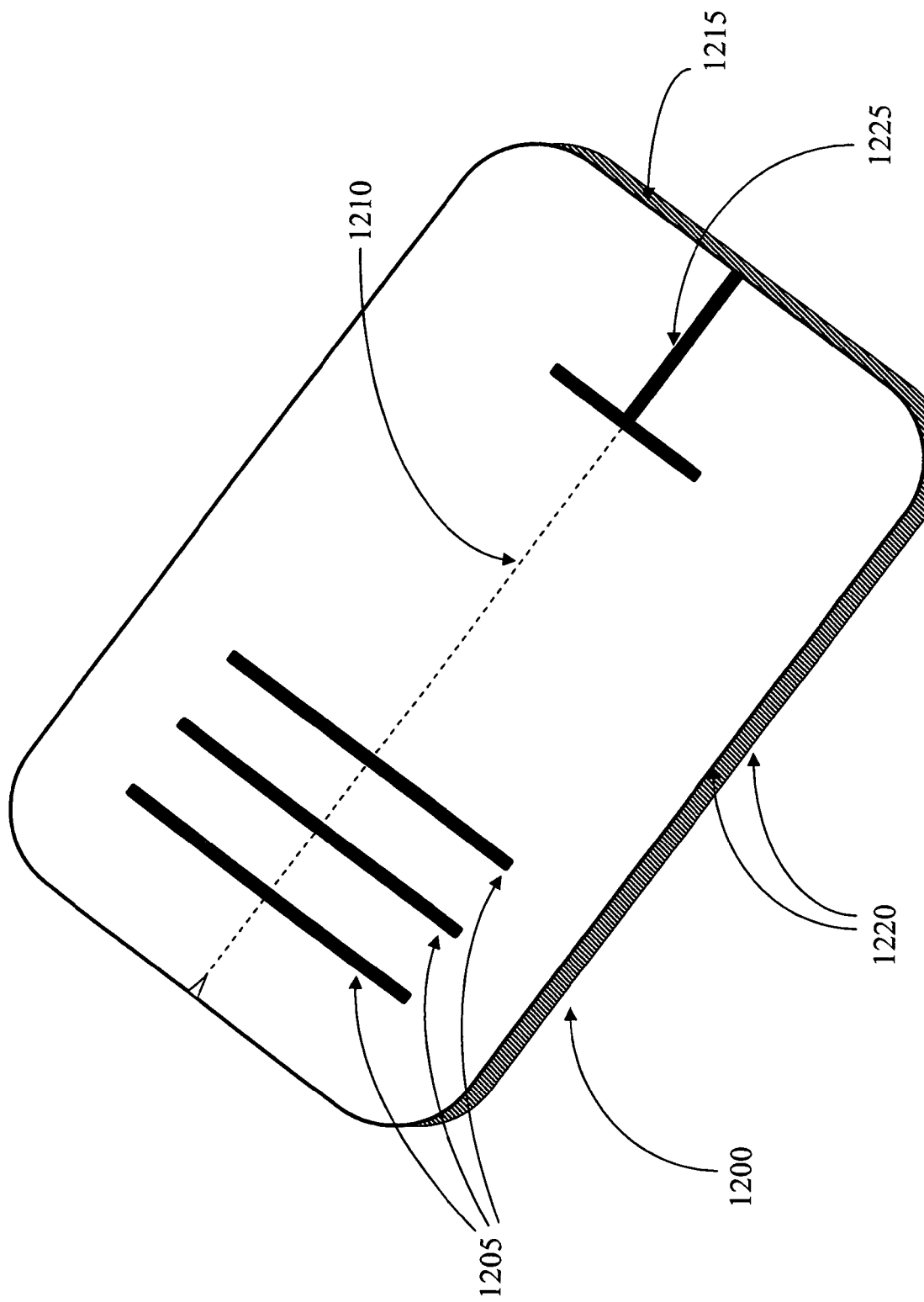
FIG. 12 is a surface view illustrating a disposable cushion that is used in conjunction with the device of the present invention.

FIG. 12, which illustrates a further feature of the present invention, is a surface view of a disposable cushion 1200 for the device 100 for emergency transport of pediatric patients. Although there are multiple alternative implementations that may be utilized, FIG. 12 illustrates a cushion 1200 made out of two individual surface layers of a paper-like or similar disposable material 1220 with a layered, compressible, absorbent, disposable material 1215 located in-between to provide padding and comfort for the pediatric patient.

The cushion 1200 is preferably made to conform to the exact dimensions of the pad 360 located in the center of the device 100 for emergency transport of pediatric patients. There are preferably a number of cut-out sections 1205 conforming to the number and dimension and alignment of the orifices 225 located on the pad where the harness restraint buckles 211 are inserted above the shoulders of the pediatric patient. Preferably, there is also a second central cut-out section 1225 located on the lower half of the cushion that conforms to the dimension and alignment of the location where the lower portion of the restraining harness 215 engages with the device 100. This second cut-out section 1225 is preferably T-shaped to allow for quick and easy placement and alignment of the cushion 1200 on the device 100 by the medical technician. The cushion 1200 optionally also has a perforation 1210 running directly down its center from top to bottom to allow it to be quickly and easily "torn-off" should life-saving measures be required.

Use of the cushion 1200 requires little to no expertise on the part of the medical technician. The medical technician either takes an individually packaged cushion or tears a cushion off of a roll. The cushion is placed on the device 100 after it is secured to the stretcher, by grasping the bottom portion of the cushion 1200 and sliding the second cut-out section 1225 around the fixed portion of the restraining harness 215 that passes through the child's legs. The child is then placed in the device 100 on top of the cushion 1200 and the restraining belt assembly is secured over the shoulders of the child by passing the harness restraint buckles 211 through first cut-out sections 1205 of the cushion and locking them directly to the device 100. Any bodily fluids secreted by the child during the transport may be captured by the cushion 1200. Should life-saving measures be required en-route, the medical technician grasps both left and right sides of the cushion 1200 and pulls. The cushion 1200 is designed to tear easily along the perforation 1210, leaving the child directly on the pad 360 where CPR and other life-saving procedures may be performed. Upon transfer of the child to a care facility, the cushion 1200 is disposed of with all other bio-related material.

Each of the devices 100 of the present invention, along with its disposable cushion 1200, provides a more effective, more sanitary, more comfortable and safer device to transport and treat children than conventional devices currently available. It operates efficiently using multiple single-action components. The device 100 also adapts to stretchers of various rail types. The design of the device facilitates the administration of various types of medical procedures, including CPR, with a child in the device. It adapts to children of various size using the restraining belt assembly 200. It facilitates the more effective treatment of a critically injured child immobilized on a backboard, as it ensures rapid access to pediatric supplies and accurate weight measurement. As a whole, medical personnel using any of the embodiments of the device 100 for emergency transport of pediatric patients and its disposable cushion 1200 are able to operate more efficiently and focus primarily on treatment instead of transport.

It will be appreciated by those of ordinary skill in the art having the benefit of this disclosure that numerous variations from the foregoing illustration will be possible without departing from the inventive concept described therein. Accordingly, it is the claims set forth below, and not merely the foregoing illustration, which are intended to define the exclusive rights of the invention.

The invention claimed is:

1. A pediatric emergency transport device comprising:
a frame consisting of (1) an upper frame section, (2) a lower frame section, and (3) at least one hinge assembly connecting the upper frame section to the lower frame section, said at least one hinge assembly enabling rotation of the upper frame section relative to the lower frame section, said upper frame section in combination with said lower frame section providing a receiving surface for receiving a pediatric patient thereupon;
an adjustable restraint assembly coupled to the frame for restraining the pediatric patient against the receiving surface during transport, said adjustable restraint assembly comprising (1) a pair of shoulder belts extending through the receiving surface of said upper frame section and longitudinally along said upper frame section, and (2) a leg belt extending along said lower frame section, wherein a position of an upper portion of each shoulder belt is adjustable along the receiving surface of said upper flame section from a front of the device so as to accommodate varying sizes of pediatric patients without removing the pediatric patient from the device; and
a pad dimensioned for placement between the receiving surface and the pediatric patient during transport, said pad extending continuously and longitudinally along said receiving surface from an upper area of said upper frame section to a lower area of said lower frame member, wherein said pad comprises (i) a cover layer that resists transfer of bodily fluids and germs from the pediatric patient onto the receiving surface of the device and (ii) slots within the pad, said slots sized so that said shoulder belts and said leg belt may extend therethrough;
said pediatric emergency transport device being operatively adapted for attachment to and detachment from a conventional stretcher;
wherein said upper frame section is pivotally hinged to said lower frame section via said at least one hinge assembly so as to be movable from (i) a first configuration wherein a first portion of the receiving surface of said upper frame section is substantially parallel to and facing a second portion of the receiving surface of said lower frame section to (ii) a second configuration wherein the first portion of the receiving surface of said upper frame section is substantially horizontal with and adjacent to the second portion of the receiving surface of said lower frame section.

2. The pediatric emergency transport device of claim 1 further comprising a removable disposable cushion that is dimensioned for placement over the pad.

3. The pediatric emergency transport device of claim 2 wherein the removable disposable cushion comprises a central perforation to allow the cushion to be torn in half and removed from beneath the pediatric patient.

4. The pediatric emergency transport device of claim 1 wherein the at least one hinge assembly comprises two separate binge assemblies.

* * * * *

UNITED STATES PATENT AND TRADEMARK OFFICE
Certificate

Patent No. 7,281,285 B2                                                                              Patented: October 16, 2007

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Stefanie A. Zucker, Atlanta, GA (US); and Suzanne J. Hantke, Plainview, NY (US).

Signed and Sealed this Twenty-seventh Day of December 2011.

*DAVID J. BAGNELL*
*Supervisory Patent Examiner*
*Art Unit 3672*
*Technology Center 3600*